United States Patent
Culver et al.

(10) Patent No.: US 10,786,156 B2
(45) Date of Patent: Sep. 29, 2020

(54) SUPER-PIXEL DETECTION FOR WEARABLE DIFFUSE OPTICAL TOMOGRAPHY

(71) Applicant: Washington University, St. Louis, MO (US)

(72) Inventors: Joseph P. Culver, St. Louis, MO (US); Karla Bergonzi, St. Louis, MO (US); Adam Eggebrecht, St. Louis, MO (US); Silvina Ferradal, St. Louis, MO (US)

(73) Assignee: Washington University, St. Louis, MO (US)

( * ) Notice: Subject to any disclaimer, the term of this patent is extended or adjusted under 35 U.S.C. 154(b) by 587 days.

(21) Appl. No.: 15/519,350

(22) PCT Filed: Oct. 16, 2015

(86) PCT No.: PCT/US2015/056014
§ 371 (c)(1),
(2) Date: Apr. 14, 2017

(87) PCT Pub. No.: WO2016/061502
PCT Pub. Date: Apr. 21, 2016

(65) Prior Publication Data
US 2017/0231501 A1  Aug. 17, 2017

Related U.S. Application Data

(60) Provisional application No. 62/065,337, filed on Oct. 17, 2014.

(51) Int. Cl.
*A61B 5/00* (2006.01)

(52) U.S. Cl.
CPC .......... *A61B 5/0073* (2013.01); *A61B 5/0042* (2013.01); *A61B 5/4064* (2013.01);
(Continued)

(58) Field of Classification Search
CPC ..... A61B 5/0059–5/0075; A61B 5/742; A61B 5/6803; A61B 5/4878; A61B 5/7207; A61B 5/0042; A61B 5/4046; A61B 5/026
See application file for complete search history.

(56) References Cited

U.S. PATENT DOCUMENTS 7,983,740 B2 * 7/2011 Culver ................. A61B 5/0042
600/476
9,480,425 B2 * 11/2016 Culver ...................... G06T 7/30
(Continued)

FOREIGN PATENT DOCUMENTS

WO      2006128889 A2    12/2006

OTHER PUBLICATIONS

Brian R. White, Quantitative Evaluation of High-Density Diffuse Optical Tomography: in vivo Resolution and Mapping Performance, 2010, Journal of Biomedical Optics, 15 (Year: 2010).*
(Continued)

*Primary Examiner* — Angela M Hoffa
(74) *Attorney, Agent, or Firm* — Armstrong Teasdale LLP

(57) ABSTRACT

A system includes a wearable head apparatus and an electronic console. The head apparatus is configured to receive resultant light from the head of a subject. The electronic console includes a fiber array, a detector, and a computing device. The fiber array includes a plurality of fibers configured to transport resultant light received by the head apparatus. The detector includes a plurality of super-pixels each defined by a plurality of pixels of an array of pixels. Each super-pixel is associated with a fiber. Each super-pixel is configured to generate a plurality of detection signals in response to detected resultant light from its associated fiber. The computing device receives the detection signals from each of the plurality of super-pixels. The computing device generates a high density-diffuse optical tomography (HD-
(Continued)

DOT) image signal of the brain activity of the subject based on the detection signals from the super-pixels.

20 Claims, 16 Drawing Sheets

(52) U.S. Cl.
CPC .......... *A61B 5/4878* (2013.01); *A61B 5/6803* (2013.01); *A61B 5/726* (2013.01); *A61B 5/7207* (2013.01); *A61B 5/742* (2013.01); *A61B 2576/026* (2013.01)

(56) References Cited

U.S. PATENT DOCUMENTS

| | | |
|---|---|---|
| 2007/0244395 A1 | 10/2007 | Wang et al. |
| 2008/0154126 A1* | 6/2008 | Culver ................ A61B 5/0073 600/426 |
| 2010/0208872 A1* | 8/2010 | Karellas .................. A61B 6/06 378/98.8 |
| 2012/0023402 A1 | 1/2012 | Cifra et al. |
| 2012/0232402 A1* | 9/2012 | MacFarlane ......... A61B 5/0075 600/473 |
| 2013/0090541 A1 | 4/2013 | MacFarlane et al. |
| 2014/0236021 A1 | 8/2014 | Islam |

OTHER PUBLICATIONS

Bergonzi et al. "Lightweight sCMOS-based high-density diffuse optical tomography". Neurophotonics 5(3), Jul.-Sep. 2018, 11 pages. (Year: 2018).*

Eggebrecht et al. "A quantitative spatial comparison of high-density diffuse optical tomography and fMRI cortical mapping." NeuroImage 61 (2012) pp. 1120-1128. (Year: 2012).*

International Search Report of International Application No. PCT/US2015/056014, dated Feb. 18, 2016, 1 page.

* cited by examiner

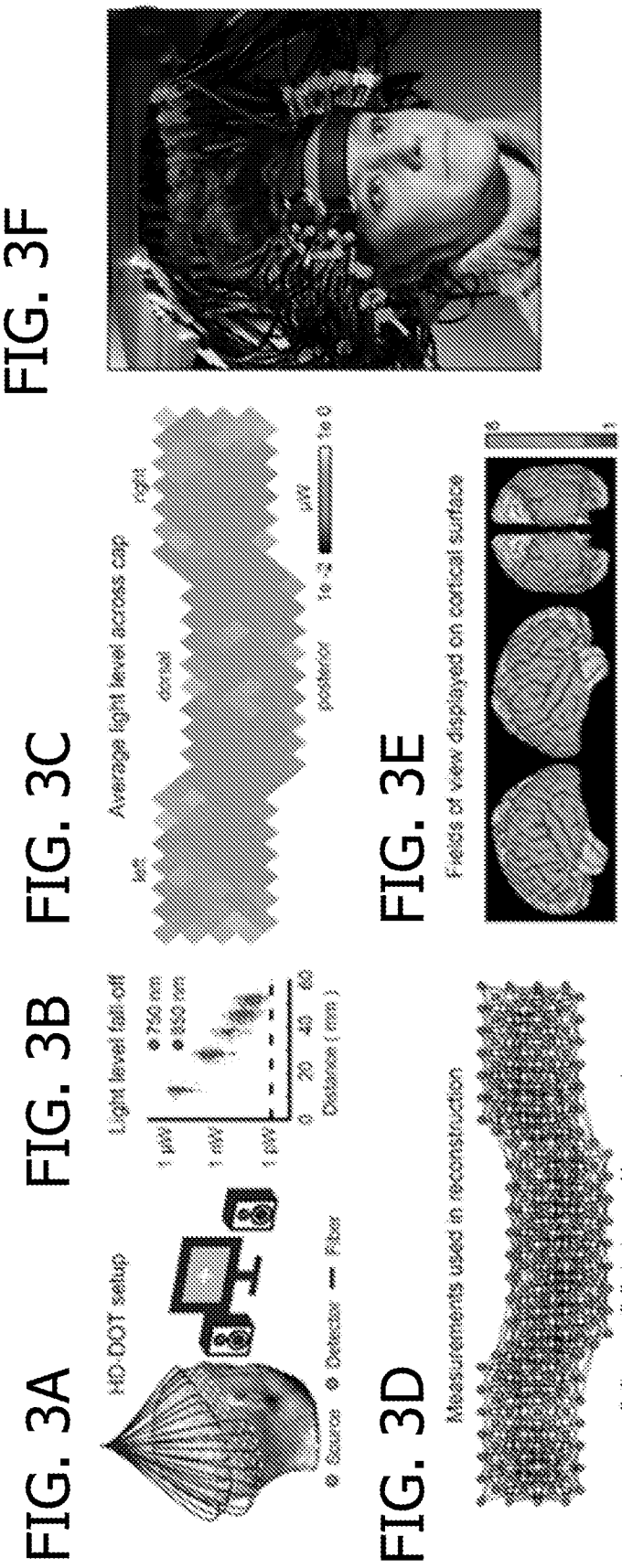

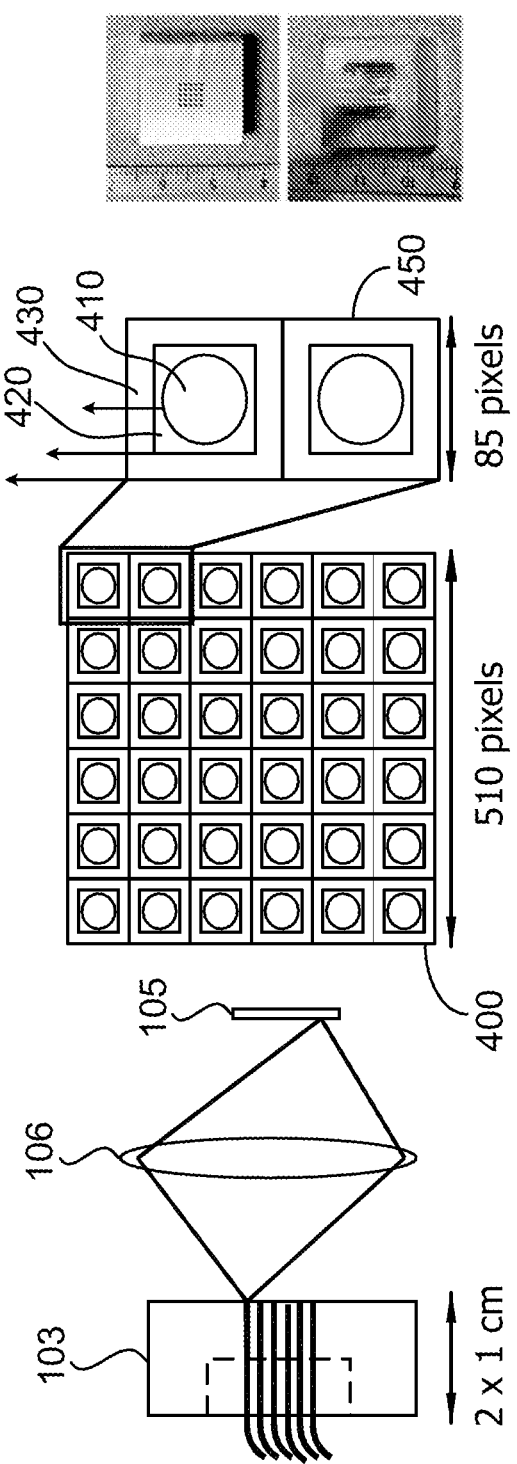

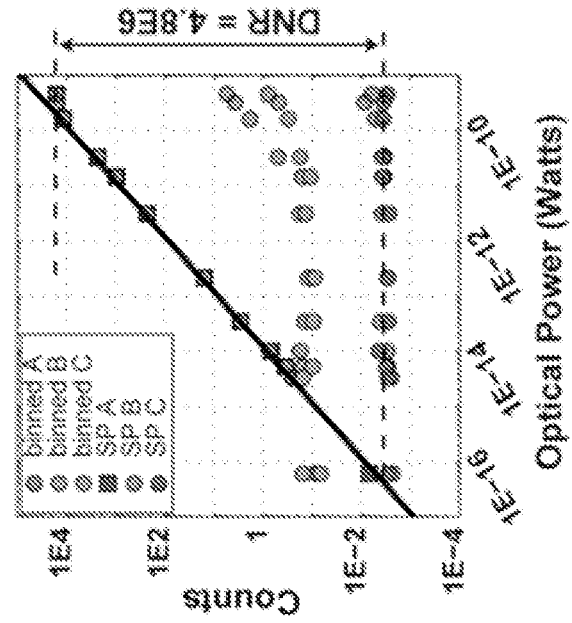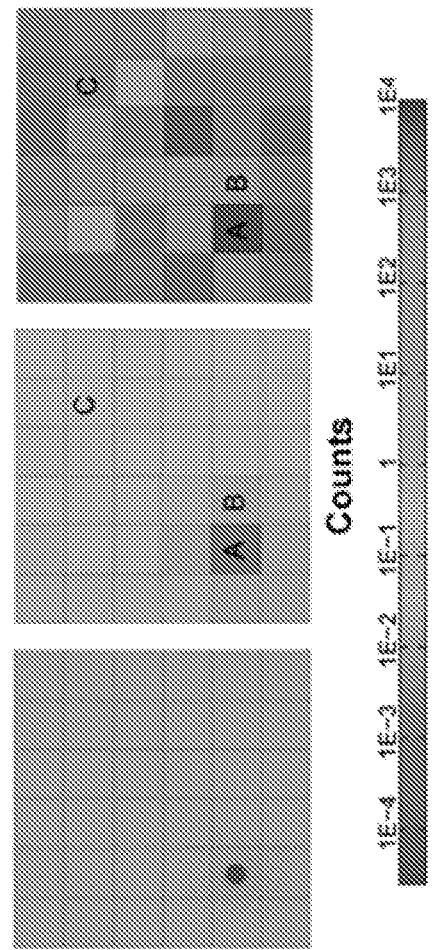
FIG. 5A raw  FIG. 5B binned  FIG. 5C super pixel (sp)  FIG. 5D

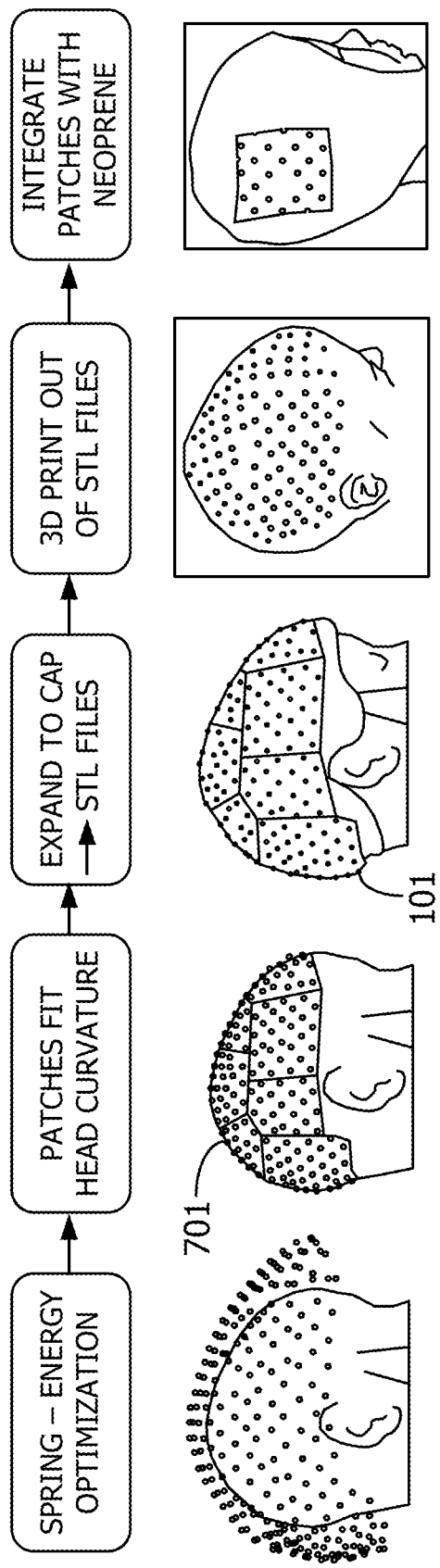

SUPER-PIXEL DETECTION FOR WEARABLE DIFFUSE OPTICAL TOMOGRAPHY

CROSS-REFERENCE TO RELATED APPLICATIONS

This application is a National Stage application of International Application No. PCT/US2015/056014, filed on Oct. 16, 2015, the entire disclosure of which is hereby incorporated by reference as set forth in its entirety. International Application No. PCT/US2015/056014 claims the benefit of priority to U.S. Provisional Patent Application No. 62/065,337, filed Oct. 17, 2014, the entire disclosure disclosures of which are incorporated herein by reference.

STATEMENT REGARDING FEDERALLY SPONSORED RESEARCH & DEVELOPMENT

This invention was made with government support under grant EB009233, awarded by the National Institutes of Health. The government has certain rights in the invention.

BACKGROUND OF THE DISCLOSURE

The example embodiments herein generally relate to measuring brain activity using diffuse optical tomography and, more specifically, to the measuring of brain activity using super-pixel detection with wearable diffuse optical tomography.

Functional neuroimaging has enabled mapping of brain function and revolutionized cognitive neuroscience. Typically, functional neuroimaging is used as a diagnostic and prognostic tool in the clinical setting. Its application in the study of disease may benefit from new, more flexible tools. Recently, functional magnetic resonance imaging (fMRI) has been widely used to study brain function. However, the logistics of traditional fMRI devices are ill-suited to subjects in critical care. In particular, fMRI generally requires patients to be centralized in scanning rooms, and provides a single "snap shot" of neurological status isolated to the time of imaging, providing a limited assessment during a rapidly evolving clinical scenario. This snap shot is generally captured on a limited basis, for example, once per stay at a hospital, once a week, once a month, and the like.

In one example, in ischemic stroke (which presents with the sudden onset of neurological deficits), the ischemia triggers a complex cascade of events including anoxic depolarization, excitotoxicity, spreading depression, and, in some cases, reperfusion. During the hyperacute phase (first hours after onset), brain injury evolves rapidly, and therapeutic interventions (e.g., thrombolysis/thrombectomy) aim to preserve viable brain tissue. Beyond the hyperacute phase, potential concerns include post-thrombolysis hemorrhagic transformation, and life-threatening cerebral edema. Therefore, throughout the hyperacute to sub-acute phases, early detection of neurological deterioration is essential and close neurological monitoring is critical.

Diffuse optical imaging (DOI) is a method of imaging using near-infrared spectroscopy (NIRS) or fluorescence-based methods. When used to create three-dimensional (3D) volumetric models of the imaged material, DOI is referred to as diffuse optical tomography, whereas two-dimensional (2D) imaging methods are classified as diffuse optical topography. Functional Near-Infrared Spectroscopy (fNIR or fNIRS), is the use of NIRS (near-infrared spectroscopy) for the purpose of functional neuroimaging. Using fNIR, brain activity is measured through hemodynamic responses associated with neuron behavior.

fNIR is a non-invasive imaging method involving the quantification of chromophore concentration resolved from the measurement of near infrared (NIR) light attenuation, temporal, or phasic changes. NIR spectrum light takes advantage of the optical window in which skin, tissue, and bone are mostly transparent to NIR light in the spectrum of approximately 700-900 nm, while hemoglobin (Hb) and deoxygenated-hemoglobin (deoxy-Hb) are stronger absorbers of light. Differences in the absorption spectra of deoxy-Hb and oxy-Hb allow the measurement of relative changes in hemoglobin concentration through the use of light attenuation at multiple wavelengths.

fNIR and fNIRS may be used to assess cerebral hemodynamics in a manner similar to fMRI using various optical techniques. In principal, fNIRS could be used for bedside monitoring of a neurological status of a patient. However, despite unique strengths, fNIRS as a standard tool for functional mapping has been limited by poor spatial resolution, limited depth penetration, a lack of volumetric localization, and contamination of brain signals by hemodynamics in the scalp and skull.

High-density diffuse optical tomography (HD-DOT) provides an advanced NIRS technique that offers substantial improvement in spatial resolution and brain specificity. However, these advancements in HD-DOT lead to additional challenges in wearability and portability. For example, by increasing a number of detection fibers in a wearable apparatus thus increasing spatial resolution, the weight of the wearable device also increases.

Accordingly, it would be beneficial to provide a new functional imaging apparatus capable of monitoring the neurological status of a patient at a bedside in a clinical setting, for example, during an acute stroke, and the like, in order to provide meaningful functional readouts useful to a clinician. Preferably, the functional imaging apparatus would be much lighter in weight in comparison to previous wearable apparatuses, and be of a size that is convenient for portability, movement, and continuous uninterrupted wearing of the apparatus. The new bedside monitoring technique would benefit patients in clinical settings such as intensive care units, operating rooms, and the like.

BRIEF DESCRIPTION OF THE DISCLOSURE

One aspect of the disclosure provides an electronic console for super-pixel detection and analysis. The electronic console includes a fiber array, a detector coupled to the fiber array, a computing device coupled to the detector, and a display. The fiber array includes a plurality of fibers configured to transport resultant light detected by a head apparatus worn by a subject. The detector is coupled to the fiber array to detect resultant light from the plurality of fibers. The detector includes a plurality of super-pixels each defined by a plurality of pixels of an array of pixels. Each super-pixel is associated with a fiber of the plurality of fibers. Each super-pixel is configured to generate a plurality of detection signals in response to detected resultant light from its associated fiber. The computing device receives the plurality of detection signals from each of the plurality of super-pixels. The computing device is configured to generate a high density-diffuse optical tomography (HD-DOT) image signal of the brain activity of the subject based on the plurality of detection signals from each of the plurality of super-pixels. The display is configured to display the HD-DOT image signal of the brain activity of the subject.

Another aspect of the disclosure provides a system with a wearable head apparatus configured to be worn on a head of a subject and an electronic console. The head apparatus is configured to direct light at the head of the subject and receive resultant light from the head of the subject in response to the light directed at the head of the subject. The electronic console includes a fiber array, a detector coupled to the fiber array, and a computing device coupled to the detector. The fiber array includes a plurality of fibers configured to transport light to the head apparatus worn by a subject and transport resultant light received by the head apparatus. The detector includes a plurality of super-pixels each defined by a plurality of pixels of an array of pixels. Each super-pixel is associated with a fiber of the plurality of fibers. Each super-pixel is configured to generate a plurality of detection signals in response to detected resultant light from its associated fiber. The computing device receive the plurality of detection signals from each of the plurality of super-pixels. The computing device is configured to generate a high density-diffuse optical tomography (HD-DOT) image signal of the brain activity of the subject based on the plurality of detection signals from each of the plurality of super-pixels.

Another aspect of the disclosure provides a computer-implemented method for performing super-pixel detection using a detector that includes a plurality of super-pixels each defined by a plurality of pixels of an array of pixels. The method is implemented by a computing device in communication with a memory. The method includes receiving, by the computing device, a plurality of detection signals from the array of pixels. For each super-pixel, a subset of the plurality of detection signals is associated with the super-pixel that generated the detection signals in the subset. A high density-diffuse optical tomography (HD-DOT) image signal of the brain activity of the subject is generated based at least in part on the subsets of the plurality of detection signals associated with the plurality of super-pixels, and the generated HD-DOT image signal is output.

BRIEF DESCRIPTION OF THE DRAWINGS

FIGS. 3A-3F are diagrams illustrating examples of a large field-of-view HD-DOT system for imaging distributed brain function;

FIGS. 4A-4C are diagrams illustrating examples of a super-pixel concept and design to decrease noise and fiber size;

FIGS. 5A-5D are diagrams illustrating examples of super-pixel detection;

FIGS. 7A-7E are diagrams illustrating an example of a second prototype of a low profile, lightweight wearable HD-DOT cap;

DETAILED DESCRIPTION OF THE DISCLOSURE

Figure 1:
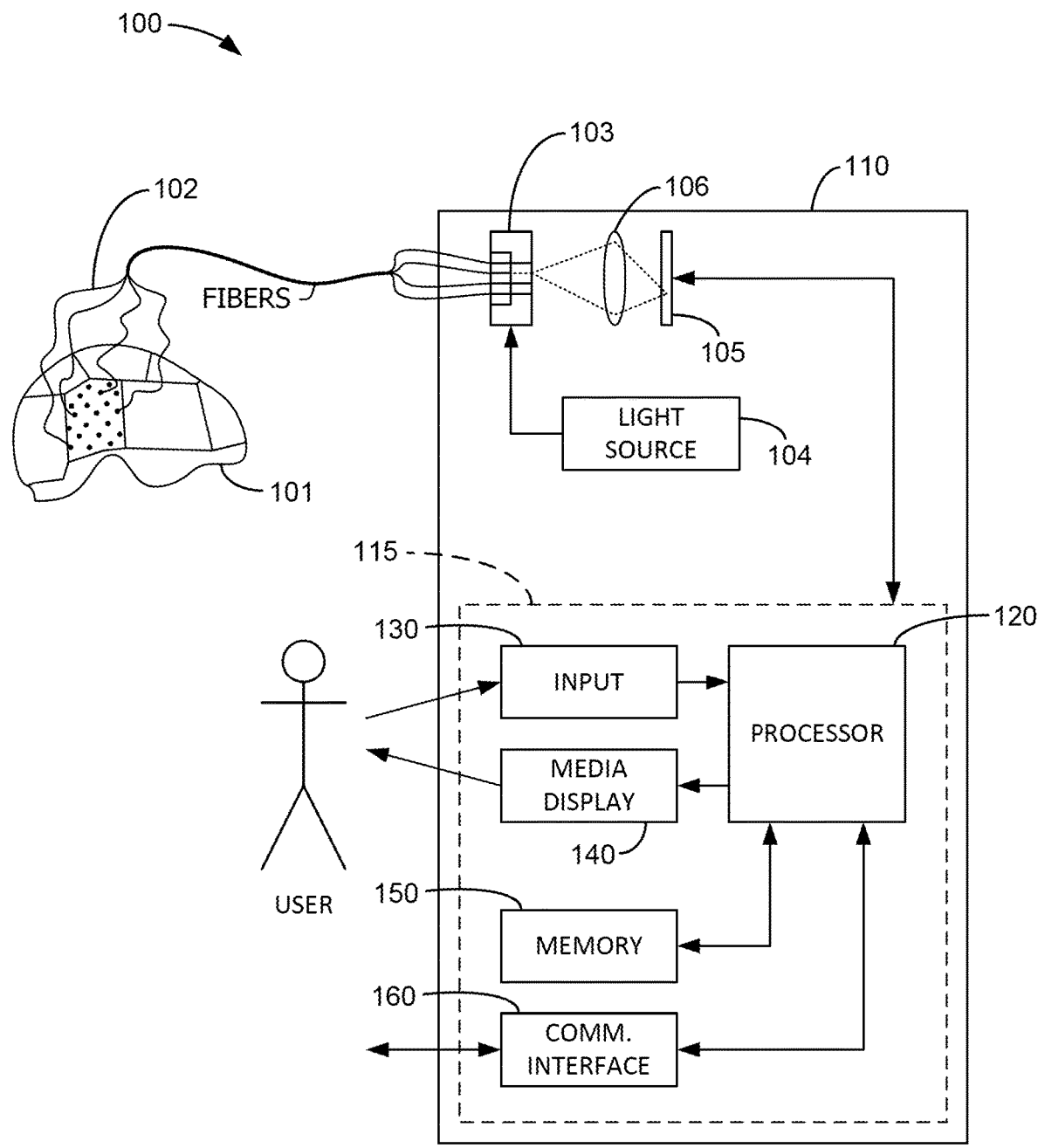
FIG. 1 is a schematic diagram illustrating an example of a high density-diffuse optical tomography (HD-DOT) system.

The example embodiments herein relate to systems, apparatuses, and methods for providing wearable, whole-head functional connectivity diffuse optical tomography (fcDOT) tools for longitudinal brain monitoring that may be used in an acute care setting, such as at a bedside of a person. For example, a wearable apparatus such as a cap, helmet, and/or the like, may be used to cover the head of the person. The cap may include fibers for detecting light reflected from the brain/head of the person. The cap may be in contact with an electronic console that may analyze the detected brain information. Also provided herein are systems, apparatuses, and methods for providing photometric head modeling and motion denoising for high density-diffuse optical tomography (HD-DOT).

According to various example embodiments, super-pixel detection enables lightweight wearable apparatuses such as caps and portable diffuse optical tomography (DOT) instrumentation. For DOT, the size of the detection fibers is an obstacle to fabricating more ergonomic (wearable) and portable DOT. For example, an average wearable HD-DOT apparatus includes approximately 280 fiber strands (about one meter in length), and has a weight of around 30 pounds. Even a sparse HD-DOT wearable apparatus having between 50-100 fiber strands has a weight that is approximately 7-10 pounds. As described in more detail, below, by introducing super-pixel detection to DOT, smaller fibers (less than about $\frac{1}{30}$ of the known standard) may be used while still maintaining HD-DOT performance specifications, and development of a novel full-head low-profile wearable DOT cap is possible.

For example, the super-pixel detection technology may use a detectors such as electron-multiply charge-coupled devices (EMCCD), scientific complementary metal-oxide-semiconductor (sCMOS) detectors, and the like. Previously developed EMCCD-based DOT systems are slow (e.g., less than about 0.01 Hz) and use geometries that may require only limited dynamic range, such as small volumes (e.g., mouse) or transmission mode measurements.

However, functional neuroimaging DOT systems have so far not used EMCCD or sCMOS technology. In the example embodiments, a super-pixel approach uses a combination of temporal and spatial referencing along with cross-talk reduction to obtain high dynamic range (DNR) and low cross talk. One improvement over previous technology such as avalanche photodiodes (APDs) is a significant reduction in sensitivity (NEP) that enables the use of smaller fibers (e.g., greater than about 30× reduction) and a smaller console (e.g., greater than about 5×).

Generally, EMCCDs and sCMOS detectors are attractive for use in DOT because they include many pixels, integrated cooling, electron multiply gain, A/D conversion, flexible software control, and the like. A challenge in using EMCCDs or sCMOS detectors is to establish DOT detector specifications, including low detection noise equivalent power (NEP<20 fW/√Hz), detectivity ($3(fW/\sqrt{Hz})/mm^2$), high dynamic range (DNR>$10^6$), low inter-measurement cross talk (CT<$10^{-6}$), and high frame rates (FR>3 Hz). However, significant challenges exist because raw single-pixel EMCCD signals fail to meet DOT specification by greater than about 100× with DNR~$10^4$, and CT~$10^{-3}$.

According to the example embodiments, the super-pixel design overcomes previous limitations of EMCCD based DOT systems and lowers the noise equivalent power (NEP) while maintaining high-dynamic range (DNR>$10^6$), low cross-talk (CT>$10^{-6}$), and reasonable frame rates (FR>3 Hz). For example, the super-pixel concept leverages massive pixel summing while avoiding corruption by noise sources.

For example, the super-pixel detection method may generate a medium sized detector (scale 0.1 to 1 mm diameter) by summing pixel values on a CMOS or CCD camera. In principal, the noise equivalent power scales as ~$area^{1/2}$, and thus (NEP/area) scales as ~$area^{-1/2}$. As a non-limiting example, a super-pixel (area=0.13 $mm^2$) may provide NEP=0.15 fW/√Hz and (NEP/area)=1.18 (fW/√Hz)/$mm^2$. However, simple binning and temporal summing may not be sufficient. EMCCDs have a dark-field signal drift that becomes apparent when summing many frames. To counter this, within frame dark-field measurements and temporal modulation/demodulation are used. By lowering the detectivity (NEP/area), the dynamic range is commensurately increased at the same time (e.g., ~$5·10^6$).

Before cross-talk is addressed, the basic math involved is addressed with super-pixel summing and how the summing modifies the noise floor, the detectivity, and dynamic range. A goal of super-pixel DOT (SP-DOT) is to create a wearable, whole-head imaging system. As a non-limiting example, the whole head may include a top half of the head, a scalp of the head, a surface of the head from the forehead to the back neckline, and the like. To achieve this, the field-standard optical fibers are decreased by a factor of ~10× in diameter. This decrease in diameter causes a ~100× decrease in weight, but also a decrease in the amount of light collected. Currently used APD detectors are not sensitive enough for use with 10× smaller fibers. Detectivity (D) is a measurement of this sensitivity per area of incident light via the fiber. Mathematically, the Detectivity is the Noise Floor (NF) of the sensor divided by the area (A) over which the light is incident.

An advantage of using sCMOS and EMCCD sensors is that they are more sensitive than the APDs. For example, the individual pixels on a sCMOS sensors have a Noise Equivalent Power (NEP) that is $10^4$ lower than the APDs. A potential drawback is that the individual pixels have a Dynamic Range that is $10^2$ lower than the APDs, and a smaller collection area. The Super-pixel algorithm shown below manipulates a CCD sensor individual pixels so that its Dynamic Range is increased while lowering the Detectivity (NEP/area).

For example, a single pixel before a super-pixel algorithm is applied has a noise floor ($NF_{pix}$), an area ($A_{pix}$), a resulting Detectivity ($D_{pix}=NF_{pix}/A_{pix}$), and a dynamic range ($DNR_{pix}$). The $DNR_{pix}$ is calculated as the full well depth of the pixel ($FW_{pix}$) divided by the noise floor: $DNR_{pix}=FW_{pix}/NF_{pix}$.

In order to increase the dynamic range and decrease the detectivity, multiple pixels are combined together by summing N pixels within a single frame together Summing N pixels together increases the full well depth linearly with N ($FW_{sp}=Fw_{pix}*N$) but the noise floor increases as the square root of N because the noise is added in quadrature ($NF_{sp}=NF_{pix}*\sqrt{N}$). The dynamic range therefore increases as the square root of N: $DNR_{sp}=FW_{sp}/NF_{sp}=(Fw_{pix}*N)/(NF_{pix}*\sqrt{N})=DNR_{pix}*\sqrt{N}$. While summing N pixels increases the noise floor, it also increases the resulting area. Therefore, the detectivity will decrease by the square root of N: $D_{sp}=NF_{sp}/A_{sp}=(NF_{pix}*\sqrt{N})/(A_{pix}*N)=D_{pix}/\sqrt{N}$.

By creating a super-pixel within a single frame, the dynamic range ($DNR_{sp}$) has increased and the detectivity ($D_{sp}$) has decreased. However to use this super-pixel algorithm for brain imaging, the sampling rate of the data needs to be considered. A typical data rate for brain imaging is 10 Hz. To compare the noise across sensors, the noise floor is calculated over a 1 second bandwidth. If the CMOS collected at a frame rate of f Hz, f images are collected per 1 second and therefore after summing over the 1 second bandwidth the noise floor and the detectivity increases as the square root off: $NF_{sp,f}=NF_{sp}*\sqrt{f}=NF_{pix}*\sqrt{N}*\sqrt{f}$.

In this example $D_{sp,f}=NF_{sp,f}/ASP=(NF_{pix}*\sqrt{N}*\sqrt{f})/(A_{pix}*N)=D_{pix}*(\sqrt{f}/\sqrt{N})$. Also, the dynamic range will be improved because "f" frames are summed: $DNR_{sp,f}=\sqrt{f}*DBR_{sp}=DNR_{pix}*\sqrt{f}*\sqrt{N}$.

Another aspect to account for in brain imaging is the encoding for location within the data. Location is encoded in separate frames, so 1 frame needs to be collected for each encoding step (K). This will have the effect of reducing the light levels in each frame by a factor of K or increasing the noise floor in each frame by a factor of K. The effective read noise will therefore increase linearly with K: $NF_{sp,f,k}=NF_{sp,f}*K=NF_{pix}*\sqrt{N}*\sqrt{f}*K$. The resultant effective detectivity will also increase linearly with K: $D_{sp,f,k}=(D_{pix}/\sqrt{N})*\sqrt{f}*K$. The dynamic range will not change as the number of frames summed does not change: $DNR_{sp,f,k}=DNR_{sp,f}=DNR_{pix}*\sqrt{f}*\sqrt{N}$.

The super-pixel algorithm therefore allows for sCMOS and EMCCD sensors to perform tomographic neural imaging by using manipulations that increase the dynamic range as compared to a single pixel and maintains a comparable detectivity by accounting for the frame rate, size of the super-pixel, and number of encoding steps.

In one example embodiment, with the super-pixel algorithm with values necessary for wearable, whole-head imaging with 200 micron diameter fibers (156× smaller and lighter than the traditional fibers (Diameter=2.5 mm)), the dynamic range of the super-pixel was reduced from 100× to only 3× lower than the APDs and the detectivity is still 10× better than the APDs (Wavelength of 690 nm, N=754 pixels, frame rate of f=10 Hz, and K=72 encoding steps).

The math in the examples above, describes the book keeping for summing across pixels and frames assuming perfect shot noise model. The cross talk reduction algorithm below will address the problem of cross-talk, a topic ignored in the math above.

Regarding cross-talk, CT is complex at multiple levels including optical focusing, and electronic sources within CCD elements, EMCCD gain, sCMOS readout structures, and A/D conversion. A super-pixel cross-talk reduction (CTR) method may be used to leverage the unique super-pixel reference areas. A bleed pattern for each super-pixel (into other super-pixels) may be measured in a calibration step. During operation, scaled bleed patterns are subtracted for each super-pixel from all other super-pixels. The bleed pattern correction is effectively a matrix operation that transforms a vector of raw super-pixel values to a vector of corrected super-pixel values. When the CTR method is implemented, the CT is less than about $1 \cdot 10^{-6}$.

The super-pixel concept generally involves two steps within frame including dark-field subtraction, and an active cross-talk reduction scheme that uses calibrated bleed patterns to remove cross-talk signals during operation based on the images obtained when multiple fibers are illuminated.

As described in more detail, below, a study was conducted for testing super-pixel feasibility. Super-pixel feasibility was tested using 0.4 mm fiber detectors. An EMCCD (Andor Tech, iXon Ultra 897) with 512×512 pixels of size 16×16 μm had an EM gain at 10×. In comparing super-pixel detectors to APDs (Hamamatsu, 3 mm dia., gain=30), NEP was evaluated at 1 Hz. Dark backgrounds were subtracted in all cases. The super-pixel detectors provide NEP=0.2 fW/√Hz, about 100× lower than the APDs, a DNR=$5 \cdot 10^6$ and CT<$10^6$. Further, the design achieves DOT frame-rates >3 Hz.

Detection fibers (400/430/730 μm core/cladding/coating, FT400EMT, Thorlabs) may be held in an aluminum block (such as a 6×6 array) and imaged onto an EMCCD. The following numbers are for a super-pixel example with a 60-pixel diameter (total ~2,826 pixels, magnification=2×).

Regarding frame-rate, with on camera binning (8×1) the camera FR=448 Hz. Each HD-DOT frame (4.1 Hz) will have a total 108 images (36 positions encode steps x [two wavelengths—690 and 850 nm—plus a dark frame]). A camera-link frame grabber with an onboard field programmable array (National Instruments NI PCIe-1473R) will compute the super-pixels in real-time super-pixel.

FIG. 1 is a diagram illustrating an example of an HD-DOT system 100 including an imaging cap 101 (sometimes referred to herein as a wearable head apparatus), a fiber array 102, and an electronic console 110 coupled with imaging cap 101 through fiber array 102.

In the example embodiment, imaging cap 101 includes a plurality of interconnected patches, each patch including a plurality of sources and a plurality of detectors. In the example embodiment, each source corresponds with a detector to define a plurality of source-detector pairs. During operation, the imaging cap 101 is placed over the patient's head, and for each source-detector pair, light is transmitted to the patient by the source. Here, the transmitted light is scattered by interactions with the patient, and at least some of the scattered light (sometimes referred to herein as "resultant light") is received by detectors. In one embodiment, imaging cap 101 is configurable for a particular patient, e.g., by modeling the cap based on the patient's anatomy, and is lightweight to facilitate portability of the HD-DOT system and enable longitudinal imaging of the patient in the acute setting (e.g., a clinic, intensive care unit, or other environment).

Fiber array 102 may include a plurality of source fibers and a plurality of detector fibers. Source fibers are optical imaging fibers that may transport light from electronic console 110 to sources on imaging cap 101. Similarly, detector fibers are optical imaging fibers that transport light from detectors on imaging cap 101 to electronic console 110. In some embodiments, fiber array 102 may be constructed using fewer and/or smaller optical imaging fibers to facilitate portability of the HD-DOT system 100.

In the example embodiment, electronic console 110 includes a fiber array holder 103, a detector 105, a lens 106 positioned between fiber array holder 103 and detector 105, and a light source 104 coupled with fiber array 102 by fiber array holder 103. Fiber array holder 103 is coupled with optical fibers (i.e., source fibers and detector fibers) of fiber array 102, and is configured to hold the fibers in a desired arrangement to allow optical communication between fiber array holder 103, detector 105, and light source 104. In the example embodiment, fiber array holder 103 holds the fibers in a square arrangement that corresponds to the shape of detector 105. In other embodiments, fiber array holder 103 may be configured to hold the optical fibers in any suitable arrangement to enable the HD-DOT system 100 to function as described herein.

Detector 105 is an image sensing device and is positioned within electronic console 110 to receive light from detector fibers of fiber array 102. Detector 105 converts incident light into electron charges to generate an electric signal that may be processed to construct, for example, HD-DOT images of the patient or the patient's brain. In the example embodiment, detector 105 may include an electron multiply charge-coupled device (EMCCD) having a plurality of pixels defined on a surface of the detector. During operation, detector fibers transport light (i.e., scattered light received by the detectors) between imaging cap 101 and electronic console 110. The light is received at the electronic console 110 at fiber array holder 103. The received light is focused onto detector 105 by lens 106, and the light incident on detector 105 is converted into an electric signal including HD-DOT image data. In some embodiments, detector 105 may include other image sensing devices such as, e.g., a charge-coupled device (CCD), a complementary metal-oxide-semiconductor (CMOS), or any suitable image sensing device to enable the system to function as described herein.

In the example embodiment of CMOS of scientific CMOS (sCMOS), the row-by-row nature of the readout by the CMOS does introduce row-specific noise. To remove temporal drift noise, the frame-to-frame background is subtracted first. If there were no other noise sources in the CMOS, the noise would follow predictions of the super-pixel math above. For the same reason the cross-talk reduction is used with the EMCCD's a similar approach is required for sCMOS. In particular it can be of an advantage to subtract row-specific noise, wherein a number of pixels for each row that are not illuminated are used to generate a row specific dark value. The row specific dark values are then subtracted from the rest of the pixels in that row.

Light source 104 is positioned within electronic console 110 to provide light to source fibers of fiber array 102. In the example embodiment, light source 104 includes a plurality of laser diodes (LDs), and each LD provides light to a source fiber and, further, to a source in imaging cap 101. In other embodiments, light source 104 includes a plurality of light emitting diodes (LEDs). In yet other embodiments, light source 104 may include any other suitable device for generating light to enable the system to function as described herein.

In the example embodiment, electronic console 110 also includes a computing device 115 for processing the electric signal generated by detector 105 to compute HD-DOT images. Computing device 115 may include at least one memory device 150 and a processor 120 coupled to memory device 150. In the example embodiment, memory device 150 stores executable instructions that, when executed by processor 120, enable computing device 115 to perform one or more operations described herein. In some embodiments, processor 120 may be programmed by encoding an operation as one or more executable instructions and providing the executable instructions in memory device 150.

Processor 120 may include one or more processing units (not shown) such as in a multi-core configuration. Further, processor 120 may be implemented using one or more heterogeneous processor systems in which a main processor is included with secondary processors on a single chip. As another example, processor 120 may be a symmetric multi-processor system containing multiple processors of the same type. Further, processor 120 may be implemented using any suitable programmable circuit including one or more systems and microcontrollers, microprocessors, programmable logic controllers (PLCs), reduced instruction set circuits (RISCs), application specific integrated circuits (ASICs), programmable logic circuits, field programmable gate arrays (FPGAs), and any other circuit capable of executing the functions described herein. Further, processor 120 may include an internal clock to monitor the timing of certain events, such as an imaging period and/or an imaging frequency. In the example embodiment, processor 120 receives imaging data from imaging cap 101, and processes the imaging data for HD-DOT.

Memory device 150 may include one or more devices that enable information such as executable instructions and/or other data to be stored and retrieved. Memory device 150 may include one or more computer readable media, such as, dynamic random access memory (DRAM), static random access memory (SRAM), a solid state disk, and/or a hard disk. Memory device 150 may be configured to store application source code, application object code, source code portions of interest, object code portions of interest, configuration data, execution events and/or any other type of data.

Computing device 115 also includes a media display 140 and an input interface 130. Media display 140 is coupled with processor 120, and presents information, such as user-configurable settings or HD-DOT images, to a user, such as a technician, doctor, or other user. Media display 140 may include any suitable media display that enables computing device 115 to function as described herein, such as, e.g., a cathode ray tube (CRT), a liquid crystal display (LCD), an organic light emitting diode (OLED) display, an LED matrix display, and an "electronic ink" display, and/or the like. Further, media display 140 may include more than one media display. According to various example embodiments, the media display may be used to display HD-DOT image data on a screen thereof.

Input interface 130 is coupled with processor 120 and is configured to receive input from the user (e.g., the technician). Input interface 130 may include a plurality of push buttons (not shown) that allow a user to cycle through user-configurable settings and/or user-selectable options corresponding to the settings. Alternatively, input interface 130 may include any suitable input device that enables computing device 115 to function as described herein, such as a keyboard, a pointing device, a mouse, a stylus, a touch sensitive panel (e.g., a touch pad or a touch screen), a gyroscope, an accelerometer, a position detector, an audio interface, and/or the like. Additionally, a single component, such as a touch screen, may function as both media display 140 and input interface 130.

Computing device 115 further includes a communications interface 160. Communications interface 160 is coupled with processor 120, and enables processor 120 (or computing device 115) to communicate with one or more components of the HD-DOT system, other computing devices, and/or components external to the HD-DOT system. Although not shown in FIG. 1, computing device 115 may further include a head modeling module that generates a photometric head model of the subject, and the detector may generate an image signal of the brain activity of the subject based on the photometric head model of the subject. Also, the computing device 115 may further include a de-noising module that removes noise from the light transported by the plurality of fibers from the head apparatus, and the detector may generate the image signal of the brain activity of the subject based on the removed noise. Embodiments of the head modeling and the noise removal are further described in various examples herein.

Figure 2:
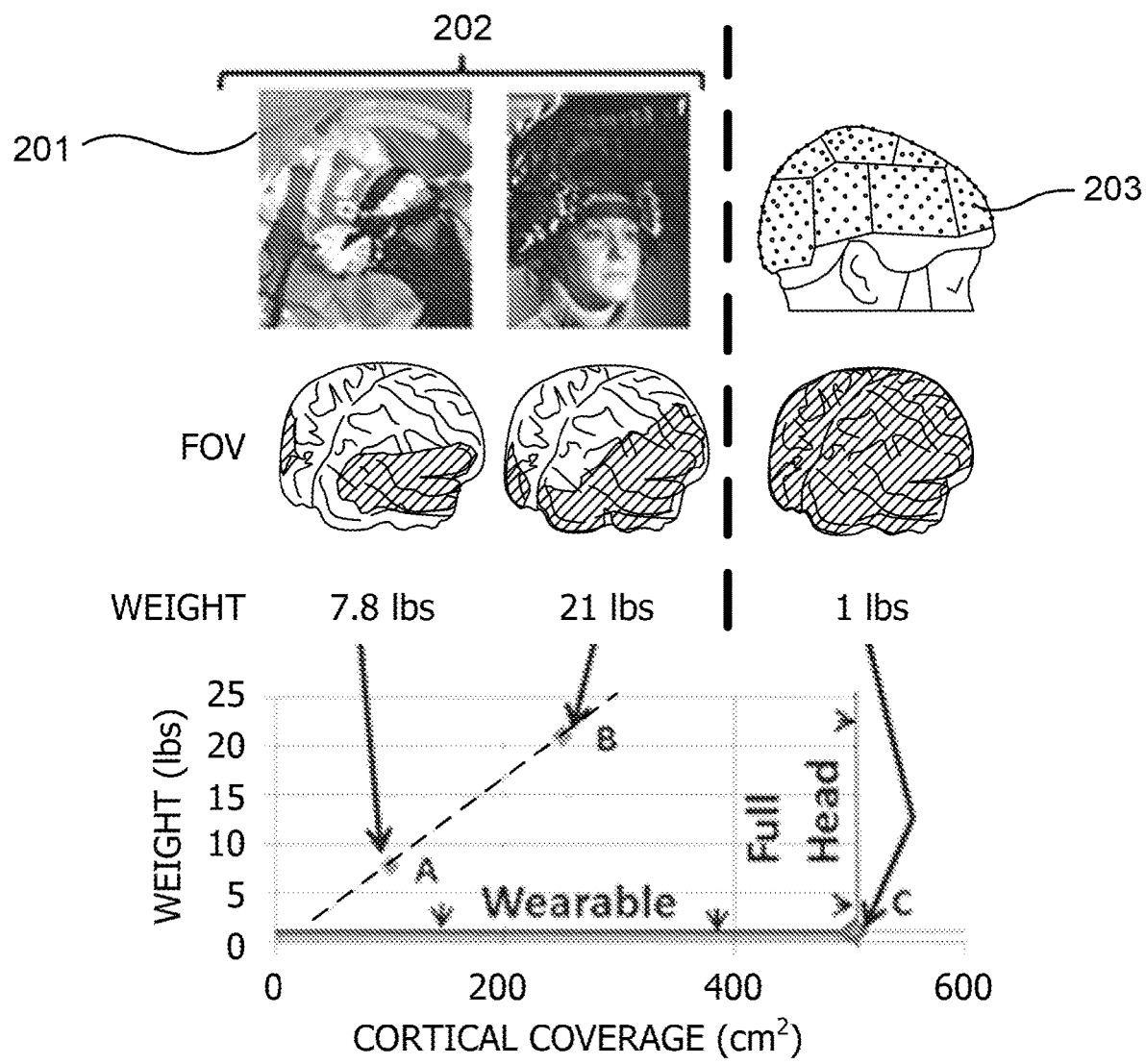
FIG. 2 is a diagram illustrating an example of a weight-vs-coverage analysis of a HD-DOT system.

In the example embodiments, HD-DOT system 100 includes imaging cap 101 that provides whole-head coverage and which is lightweight. FIG. 2 illustrates an example of a weight-vs-coverage analysis of an HD-DOT system including wearable head apparatuses having different coverages and weights. As shown in FIG. 2, at point A, sparsely populated HD-DOT systems are lightweight (or wearable), but do not provide whole-head coverage. In this example, wearable head apparatus 201 includes sparsely populated fibers that, when combined, weigh approximately 8 pounds. However, due to the space between each fiber, the apparatus 201 does not provide complete coverage of the entire head of a person.

Coverage may be increased to provide whole-head imaging by increasing the number of source-detector pairs in the imaging cap, and increasing the relative number of imaging fibers coupled with the imaging cap. In such systems, increasing the number of imaging fibers also increases the weight of the imaging cap. As shown in FIG. 2 at point B, increasing coverage by increasing the number of imaging fibers in wearable head apparatus 202, forces the use of "hair-dryer" ergonomics for approximately one-half head coverage (also shown in FIG. 3). In this example, more head coverage is provided, however, such coverage requires about 280 fibers (for 1 m length fibers) and weighs up to about 30 lbs. Although the wearable head apparatus in this example can be supported by strain-relief guides, this fixes the apparatus in space and requires special seating and positioning that result in the "hair-dryer" ergonomics. Moreover, the electronic console in this system typically requires three 7 foot, 19 inch racks, and is essentially not portable. As a non-limiting example, a length of the fibers may be in a range between zero and two meters, one half meter and one and a half meters, one meter to three meters, and the like.

As shown in FIG. 2 at point C, wearable whole-head HD-DOT 203 according to one or more example embodiments may be provided by reducing the weight of a wearable head apparatus (i.e. an imaging cap in this example) while maintaining, or enhancing, head coverage. For example, during operation, a wearable whole-head HD-DOT apparatus 203 can meet (or exceed) performance requirements imposed by the high attenuation (blood volume) of the brain with optode separations of about 1-5 cm. Performance requirements may include low noise levels (NEP<20 $fW/\sqrt{Hz}$ for a 3 mm detector), high dynamic range (DNR>$10^6$), and low inter-measurement cross talk (CT<10).

In this example, a super-pixel approach to instrumentation enables weight reduction of HD-DOT imaging caps. For example, a wearable whole-head HD-DOT apparatus 203 is enabled, at least in part, by using a super-pixel detection method and electron-multiply charge-coupled devices (EM-CCD). The super-pixel detection method uses a combination of temporal and spatial referencing along with cross-talk reduction to obtain high dynamic range (DNR) and low cross talk. Furthermore, the super-pixel detection method provides a reduction in sensitivity (NEP) over at least some known methods and enables the use of smaller imaging fibers and a smaller console. For example, the method enables the use of imaging fibers up to about 30 times smaller than such fibers for known methods, and enables the use of an electronic console up to about 5 times smaller than such consoles for known methods. In one embodiment, use of smaller imaging fibers provides an imaging cap having a weight of about 1 lb (e.g., similar to the weight of a bicycle helmet) which, when provided along with an electronic console having a low-profile design, provides a wearable whole-head HD-DOT system suitable for longitudinal fcDOT in the acute care setting. In addition, whole-head HD-DOT apparatus 203 extends the field-of-view to cover multiple contiguous functional domains. For example, the imaging cap may have a weight between 0 pounds and two pounds, a range between a half pound and one and a half pounds, and the like. As another example, the imaging cap may have a weight that exceeds two pounds or that is less than two pounds.

FIGS. 3A-3F are diagrams illustrating examples of a large field-of-view (FOV) HD-DOT system for imaging distributed brain function. The examples of FIGS. 3A-3F correspond to wearable head apparatus 202 in FIG. 2. In the example embodiments, FIG. 3A illustrates a set-up for HD-DOT. FIGS. 3B, 3C, and 3D illustrate a plurality of monitored data sets for managing data quality control. For example, FIG. 3B illustrates the average light intensity for every source-destination (SD) pair separated by <55 mm, spanning a $DNR=10^6$. FIG. 3C illustrates an average light level for each source and detector on a flattened view of the cap. FIG. 3D illustrates measurements above the noise threshold (variance <7.5%, shown as lines). Also, FIG. 3E illustrates the FOV across 8 subjects, where color bar codes the number of subjects with usable sensitivity at a given location of cortex. FIG. 3F illustrates a subject wearing a fiber head apparatus.

In the prototype HD-DOT system of FIGS. 3A-3F, DOT instrumentation for improved cortical coverage was developed by constructing a high-density array including a high-density regular grid of sources and detectors. The high-density array places strong demands on hardware, specifically, high sensitivity, low noise floor, and large dynamic range of each detector (shown in FIG. 3b). Development of in situ data quality control was critical for managing the large source-detector pair data sets (# SD-pairs>2000) (shown in FIGS. 3C and 3D). An imaging head apparatus was developed that couples the optodes (i.e., source and detector fibers) to the head. However, in this example, the head apparatus is very heavy due to the size of the fibers included in the source-detector array.

According to various example embodiments, super-pixel concepts and designs may be applied to the optical fibers and image sensors of the HD-DOT systems described herein, enabling a reduction in an overall size of the wearable head apparatus, and, thus enabling a reduction in a size of a computing device that the head apparatus is connected to.

FIGS. 4A-4C are diagrams illustrating examples of a super-pixel concept applied to an HD-DOT system to decrease noise and fiber size. Referring to FIG. 4A, the fibers are relayed to an electron multiply charge coupled device (EMCCD) 105 using a high numerical aperture lens to maintain high transmission (e.g., >90%). As shown in FIG. 4B, a 6×6 array of super-pixels 400 is defined. Each super-pixel 450 of the array of super-pixels 400 includes a core region 410 used to detect the super-pixel light intensity, a buffer region 420 where light levels decay by up to $10^4$ and are discarded, and a reference region 430 to calculate stray noise signals. Using reference subtraction, very low noise and cross talk may be obtained (shown in FIG. 5). FIG. 4C illustrates a front view of a fiber array holder (top) and a back view with optical fibers (bottom).

In the example embodiments, a super-pixel detection method may overcome previous limitations of CCD-based DOT systems. Also, the super-pixel detection method may lower the noise equivalent power (NEP) relative to avalanche photodiode (APD) detection (NEP=20 fW/√Hz), while maintaining high-dynamic range (DNR>$10^6$), low cross-talk (CT<$10^{-6}$), and reasonable frame rates (FR>3 Hz). The super-pixel detection method leverages pixel summing while reducing corruption by noise sources. When implementing the super-pixel detection method, a cross talk reduction (CTR) method between super-pixels may be performed. A study was conducted to test the feasibility of the super-pixel detection method using 0.4 mm fiber detectors (shown in FIGS. 4 and 5). In the study, the image sensor included an EMCCD with 512×512 pixels of size 16×16 μm had an EM gain at 10×.

In the example embodiments herein, a super-pixel such as super-pixel 450 shown in FIG. 4B includes a plurality of pixels combined to form one large super-pixel. In the example of FIGS. 4A-4C, a detector 400 includes an array of pixels. In this example, the detector includes an array of 510×510 pixels. Rather than analyze data from each individual pixel, the example embodiments generate the super-pixels. In this example, a super-pixel is 85×85 pixels. Accordingly, rather than an array of pixels including 260,100 pixels (510×510), the array includes 36 super-pixels (6×6), where each super-pixel includes 7,225 pixels. It should be appreciated that the example embodiments are not limited to specific sizes of detector arrays 400 and super-pixels, and may be any desired size.

Within each super-pixel is a pixel core 420. The pixel core may include a square shape, a circular shape, an oval shape, an elliptical shape, and the like. In various examples, to prevent noise and cross-talk between super-pixels, each super-pixel 450 includes a buffer 420 that surrounds the pixel core 410. Also, buffer 420 may be further surrounded by reference region 430. For example, the buffer 420 and the reference region 430 may be generated by turning off or otherwise preventing light from being detected by pixels in the buffer region 420 and the reference region 430. In this example, the pixel core 410, the buffer region 420, and the reference region 430 may be included within the super-pixel (i.e. within the 85×85 pixels).

FIG. 5 are photographs illustrating a performance of the super-pixel detection method (all data is shown as log(abs(data))) shown in FIG. 4. As shown in FIG. 5A, raw EMCCD images have a DNR that is determined by the full well capacity and the readout noise for about $10^4$. As shown in FIG. 5B, simple binning into 6×6 binned regions improves the DNR to $1×10^5$, but cross talk still occurs at $1×10^{-3}$. As shown in FIG. 5C, super-pixel analysis reduces CT<$10^{-6}$ and generates a DNR of about $5×10^6$, and NEP=2 fW/√Hz. FIG. 5D illustrates a full range test showing improved CT and DNR of super-pixels versus simple binning.

In the example of FIGS. 5A-5D, in studying the feasibility of the super-pixel detection method, the super-pixel detection method is compared to a design including avalanche photodiodes (APDs) (Hamamatsu, 3 mm dia., gain=30) by evaluating NEP at 1 Hz. In this example, dark backgrounds were subtracted in all cases (shown in FIGS. 5A, 5B, and 5C). Based on the comparison, the super-pixel detection method provides NEP=0.2 fW/√Hz, 100× lower than the design including APDs, a DNR=5×10$^6$, and CT<10$^6$. Further, the super-pixel detection method achieves DOT frame-rates less than about 3 Hz. Yet further, the super-pixel detection method also enables improvements in wearability.

According to various example embodiments, imaging caps used in various examples were developed using the super-pixel detection method for use in the acute setting.

Figure 6A:
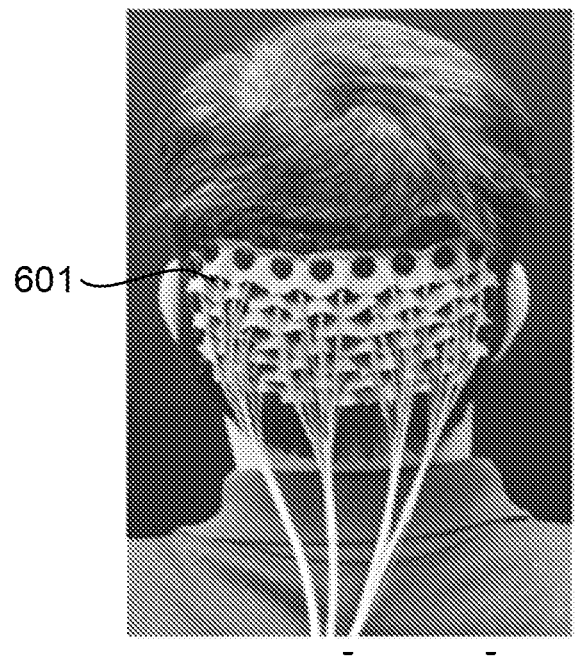
FIGS. 6A-6B are diagrams illustrating an example of a first light weight prototype cap.
Figure 6B:
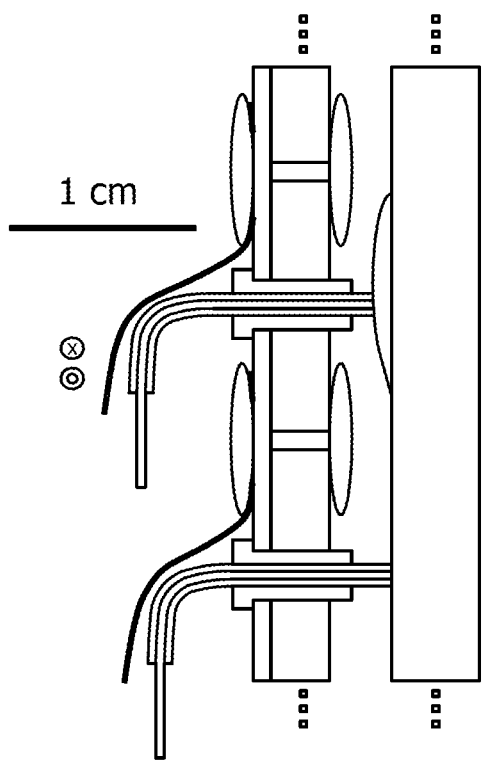

FIGS. 6A-6B illustrate examples of an HD-DOT imaging cap 601. As shown in FIG. 6A, HD-DOT imaging cap 601 includes 24 source fibers and 28 detector fibers. FIG. 6B illustrates an example of the elastic fiber attachment of HD-DOT imaging cap 601 for facilitating lateral stability and surface normal compliance. HD-DOT imaging cap 601 may be built using super-pixel lightweight fibers to provide improvements in cap ergonomics. In HD-DOT imaging cap 601, fibers may be epoxied within right-angle aluminum tubes and are anchored to the cap with elastic straps that provide a "spring" effect to hold the fibers firmly yet comfortably against the scalp (shown in FIG. 6A). The fibers and/or tubes may protrude through the cap by about 3-5 mm allowing for combing through hair of a person. In this example, for a whole-head wearable cap, approximately 288 fibers have a total cross-sectional area of about 1.4 cm$^2$, similar to four USB cables.

FIGS. 7A-7E illustrate a second prototype HD-DOT imaging cap 701 that is a low profile, lightweight wearable HD-DOT imaging cap. As shown in FIGS. 7A and 7B, fibers of second prototype imaging cap 701 are guided by an anatomical computer model that optimizes the placement of the fibers, and accommodates the position dependent curvature of the head surface (which may be generated from a MRI population atlas). As shown in FIGS. 7C and 7D, a head surface is expanded to a cap 8 mm larger than the head, and converted to STL files which are printed in ABS plastic using a three-dimensional (3D) printer. As shown in FIG. 7E, the patches are integrated into a neoprene cap. Elastic fiber management from HD-DOT imaging cap 601 (shown in FIG. 6) is incorporated to optimize fiber/scalp coupling.

In designing the second HD-DOT imaging cap 701, second imaging cap 701 incorporates anatomical morphology of the head (derived from MRI data) into the cap structure itself. Using an energy minimization algorithm, the full-head grid of optode positions may be relaxed onto a computer model of a subject's head anatomy (shown in FIG. 7A) while maintaining an interlaced source and detector grid topology. The computer model is divided into 9 patches of optodes (shown in FIGS. 7B and 7C) that provide local stability of the cap and assist in fiber management. The patches were realized with a three-dimension printer (shown in FIGS. 7D and 7E) and were attached to a neoprene cap to provide comfort and flexibility between the patches through hinge mechanisms (shown in FIG. 7E). In building the second HD-DOT imaging cap 701, the super-pixel lightweight fibers de-couple the goals of cap deformation (elastic fiber management and neoprene patch hinges) from fiber torque (less flexible ABS plastic patches).

According to various example embodiments, an HD-DOT system includes a wearable, whole-head HD-DOT for clinical based brain imaging using the super-pixel detection method described herein. In various examples, wearable HD-DOT includes an imaging cap weight of about 1 lb. Imaging fiber weight is largely determined by the area of the fiber for light collection. One of the challenges in reducing the size of a fiber is maintaining HD-DOT specifications. For example, HD-DOT specifications include low detection noise equivalent power (NEP<20 fW/√Hz, dia=3 mm, NEP/mm$^2$~2.8(fW/√Hz)/mm$^2$), high dynamic range (DNR>106), low inter-measurement cross talk (CT<10$^{-6}$), and high frame rates (FR>3 Hz). Super-pixel detection methods enable generating an about 0.4 mm diameter detector by summing pixels on a CCD camera. Generally, EMCCDs are attractive for DOT with many pixels, integrated cooling, electron multiply gain, A/D conversion and flexible software control. However, additional challenges exist because raw single-pixel EMCCD signals fail to meet HD-DOT specifications by greater than 100× with DNR~10$^4$, and CT~10$^{-3}$.

Super-pixel detection methods help solve these challenges as shown in Table 1, below, and FIGS. 4 and 5. Detection fibers (400/430/730 μm core/cladding/coating, FT400EMT, Thorlabs) are held in an aluminum block (6×6 array) and imaged onto an EMCCD. The following numbers are for a super-pixel with a 60-pixel diameter (total about 2826 pixels, magnification=2×). Since NEP scales as about area$^{1/2}$, NEP per area scales as about are$^{-1/2}$, Potentially, a super-pixel (area=0.13 mm$^2$) provides NEP=0.15 fW/√Hz and NEP per area=1.18 (fW/√Hz)/mm$^2$. However, as shown in FIG. 5, simple binning and temporal summing is not sufficient. EMCCDs have a dark-field signal drift that becomes apparent when summing many frames.

Within frame, dark-field measurements and temporal modulation and/or demodulation may be used to counter signal drift. For a super-pixel (dia=0.4 mm), the effective noise/area is reduced by about 50 and the dynamic range reaches about 5×10$^6$. CT is complex at multiple levels including optical focusing, and electronic sources within CCD elements, EMCCD gain and A/D conversion. A super-pixel cross-talk reduction (CTR) method was developed, leveraging the unique super-pixel reference areas (shown in FIG. 4). The bleed pattern for each super-pixel (into other super-pixels) is measured in a calibration step. During operation, scaled bleed patterns are subtracted for each super-pixel from all other super-pixels. After CTR, the CT is less than 1×10$^{-6}$ (shown in FIG. 5). With on-camera binning (8×1) the camera FR=448 Hz. Each HD-DOT frame (4.1 Hz) includes a total 108 images (36 position encode steps × [two wavelengths—690 and 850 nm—plus a dark frame]). A camera-link frame grabber with an onboard field programmable array (National Instruments NI PCIe-1473R) computes the super-pixels in real-time.

TABLE 1

| Detector Approach | weight (lbs) | area (mm$^2$) | NEP/Area (fW/√Hz)/mm$^2$ | Dynamic Range | Cross talk |
| --- | --- | --- | --- | --- | --- |
| APD | 30 | 7.1 | 2.8 | 1E+07 | 1E−06 |
| EMCCD-binned | 1 | 0.13 | 50 | 1E+05 | 1E−03 |
| EMCCD-super-pixel | 1 | 0.13 | 1.18 | 4.8E+06 | 1E−06 |

The example system includes illumination sources including laser diodes (LD), providing an about 30× increase in peak light level (60 mW vs. 2 mW CW power) over light emitting diodes (LEDs). For example, individual LDs (670 nm RL67100G, 850 nm R85100G, Roithner-Lasertechnik) for each source position may be coupled to 200 μm fibers. On the scalp, diffusing elements provide about a 2.5 mm spot. At a 1/10$^8$ duty cycle, the single source fluence is about 0.2 mW/mm$^2$, well below the ANSI limit (4 mW/mm$^2$).

The example system also includes an electronic console including a camera, lens, and fiber coupling block occupying about 6×8×8 inches (height x width x depth). In a 10U height (19 in rack), 144 super-pixel detectors are included with about 5× compression compared to known APD-DOT (50U for 144 detectors). Illumination will use 9U. The full system is about 36×48×24 inches, including a computer (control, collection, processing).

The example system further includes an imaging cap (shown in FIGS. 6A and 7A-7E) including sub-arrays of 6×6 detectors interlaced with 6×6 sources, with 36 step time encoding of the sources. The resulting four sub-arrays run concurrently since the active sources are separated by a distance greater than 2× the longest usable source-detector pair ($5^{th}$ nearest-neighbor) distance. In developing the imaging cap, the model may be guided by an anatomical computer model that optimizes the placement of fibers and accommodates the position dependent curvature of the head surface (shown in FIGS. 6 and 7). To accommodate the wide range of head sizes, the HD-DOT imaging cap may be configured in small (53±2 cm), medium (57±2 cm) and large (61±2 cm) caps. The caps may be optimized using small pilot studies.

The example system may also include real-time displays for cap fit optimization. According to various aspects, HD-DOT performance depends critically on fiber/scalp coupling. To guide operator cap fit, real-time displays may be developed and used in both "measurement space" (shown in FIGS. 3C and 3D) and image space using a graphics processing unit cluster (e.g., an NVidia Tesla C2075 GPU cluster). For example, developed real-time displays may be used to estimate real-time imaging within about 1 minute of cap placement.

To test the example HD-DOT system, bench top and in vivo performance tests may be conducted. Tests with the full implementation of a super-pixel DOT system may be used to confirm the system specifications (shown in Table 1). In vivo tests provide realistic cranial tissue structures and subject movement. Initial prototype testing may include longitudinal wearability testing for up to about 12 hour scan times (20 minute breaks every 4 hours, shown in FIG. 15). Functional imaging in healthy adults (N=20) for visual, auditory, and language tasks and rest is enabled by methods similar to those shown in FIGS. 12A-12D, and 13A-13F.

In further testing of the example HD-DOT system, the parameter space of the system may be analyzed to meet design goals. According to various aspects, a strength of the system is its extensive flexibility, with regard to the pixel binning, detector size, and temporal summing, which may optimize the field-of-view, dynamic range and speed. Particularly, the system may be analyzed to determine the most relevant real-time displays for cap fit. Further, the system may be analyzed to determine the relative importance of "sensor space" vs "image space" data with respect to cap fit. The analysis (and other appropriate feedback) may be used to develop real-time displays for the system.

In some example embodiments, photometric head modeling and motion denoising for high density-diffuse optical tomography (HD-DOT) may be used in at least some of the examples.

In providing wearable, whole-head HD-DOT for the acute setting using systems such as, e.g., the example HD-DOT system, the subject's head surface and the position of the imaging cap are captured for registering the DOT data set to a model of the subject's anatomy. Some known cases have demonstrated the advantage of using co-registered anatomical head modelling to improve HD-DOT localization. Specifically, demonstrating the use of individual subject anatomical MRI (shown in FIGS. 2, 3, and 8). However, for the acute care setting, research quality MRIs may not be available for many subjects, and head models may be generated by transforming reference (or atlas) anatomy to the subject. Computing an individual light-path model requires capturing the exterior shape of the head and the relative location of the HD-DOT imaging cap. A photometric approach is contemplated for efficiently capturing this data, where non-linear models are used to obtain an about 5 mm correspondence with fMRI. Preliminary tests of the contemplated approach show that non-linear registration may be used to obtain localization errors of less than about 3 mm for reference-anatomy versus subject-MRI head models (shown in FIGS. 9A-9E).

The next challenge is de-noising the captured data for the subject's head surface and the position of the cap from motion artifacts. Some known methods, including independent component analysis (ICA) and wavelets, have been evaluated for fMRI and (NIRS, but have yet to be established for fcDOT. HD-DOT overlapping measurements impose an inherent structure on potential fiber movement induced error signals. A method is contemplated that uses HD-DOT overlapping measurements to quantify optode coupling and provide mathematical correction of the raw signal to account for movement artifact. A study will be conducted to evaluate the contemplated method against known approaches such as ICA and wavelet approaches.

In creating DOT head modeling and spatial normalization of functional brain maps, improvements in instrumentation (shown in FIG. 2) prompted the need for advancements in (i) realistic forward light modeling for accurate HD-DOT image reconstruction and (ii) spatial normalization for voxel-wise comparisons across subjects.

Figure 8:
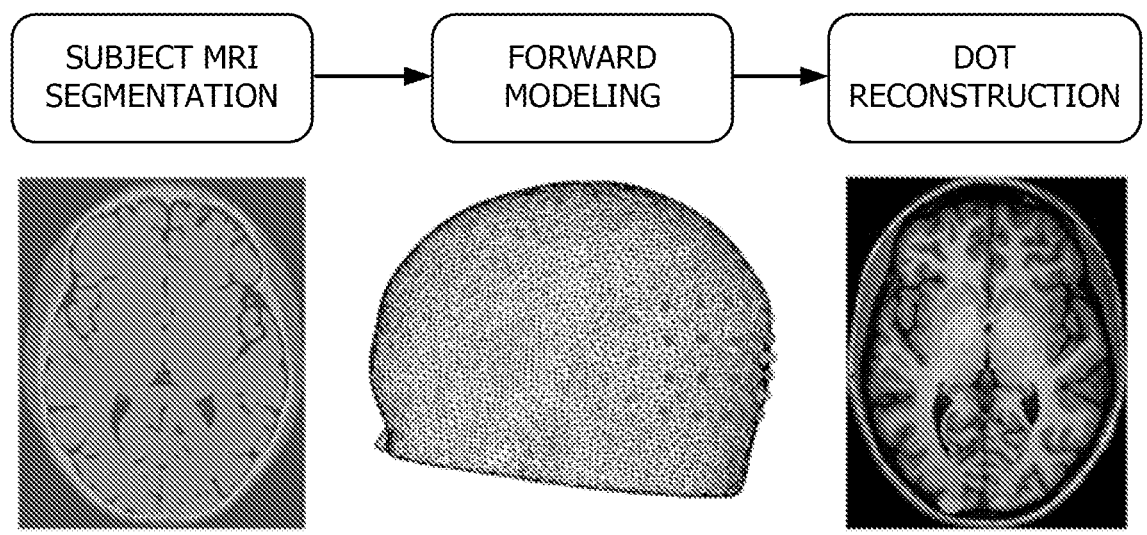
FIG. 8 is a flow diagram illustrating an example for improving HD-DOT using anatomical reconstructions.
Figure 9:
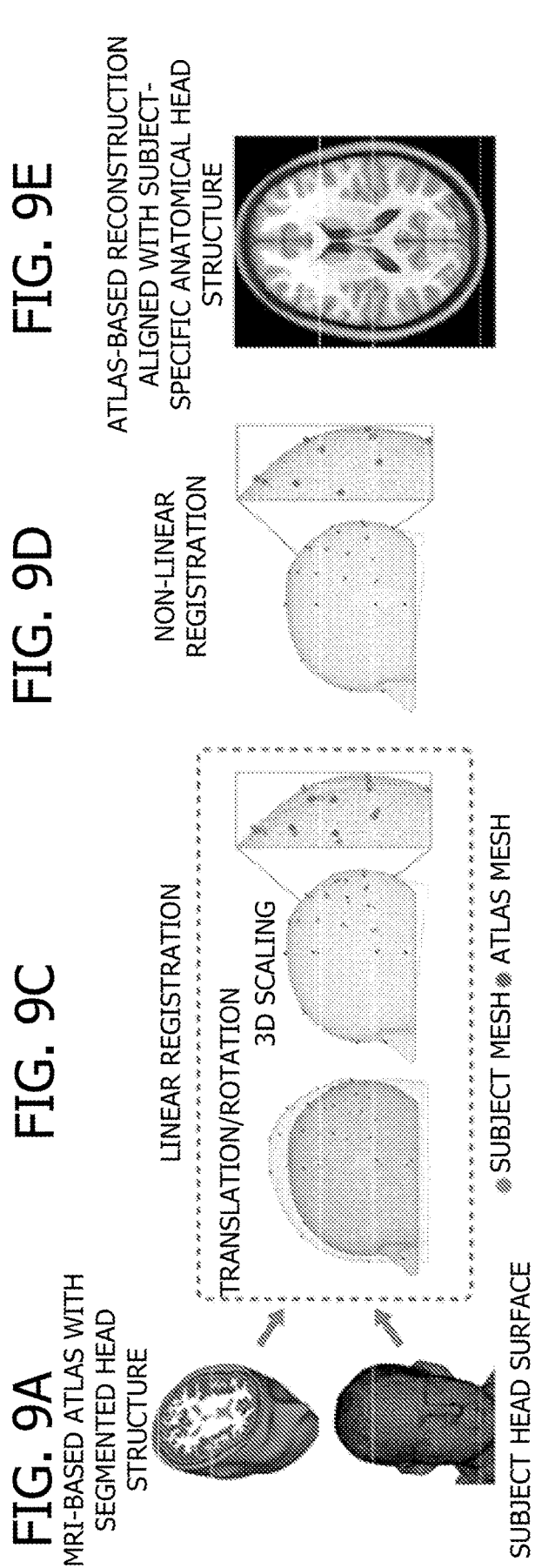
FIGS. 9A-9E are diagrams illustrating examples of head surface driven subject-specific head modeling.

FIG. 8 are photographs illustrating example anatomical (e.g., subject MRI) reconstructions for improving HD-DOT. As shown in FIG. 8, a processing pipeline for anatomically based forward light modeling and spatial normalization was developed. A study was conducted to validate both methods in five healthy adults by direct comparison of HD-DOT vs. fMRI responses to visual stimuli (shown in FIG. 12). At the group level, the localization error of DOT relative to fMRI was about 6.1 mm. Co-registration to anatomy also enabled projection to the pial cortical surface using Computerized Anatomical Reconstruction Toolkit (CARET), an fMRI processing tool (shown in FIG. 12).

In the acute care setting, subject MRI may be unavailable for creating anatomically accurate head models. FIGS. 9A-9E are photographs illustrating head surface driven subject-specific head modeling for creating anatomically accurate head models without subject MRI. As shown in FIGS. 9A-9E, reference anatomy is transformed to the subject head surface using linear and non-linear optimizations, and the output is subject specific DOT.

In the example embodiment, as shown in FIGS. 9A-9E, anatomically accurate head models are created using reference anatomy (population MRI data) (shown in FIG. 9A) that is warped to each individual head surface (shown in FIG. 9B) using two consecutive fitting routines. The fitting routines include a linear registration for performing global adjustments (shown in FIG. 9C), and a non-linear registration for improving local fitting (shown in FIG. 9D). In the example embodiment, input is received including the external surface of a subject's head, the location of the optode array relative to the subject's head, and a set of anatomical fiducials used in the registration routines. The warped atlas and the co-registered optode array are used to compute an individualized forward light model that is aligned with the subject's anatomical head structure (shown in FIG. 9E). The premise of atlas-based head modeling is validated using head surfaces extracted from subject MRI scans and by comparing to DOT reconstructions using subject-specific anatomical images and to subject-matched fMRI datasets (shown in FIG. 10).

Figure 10:
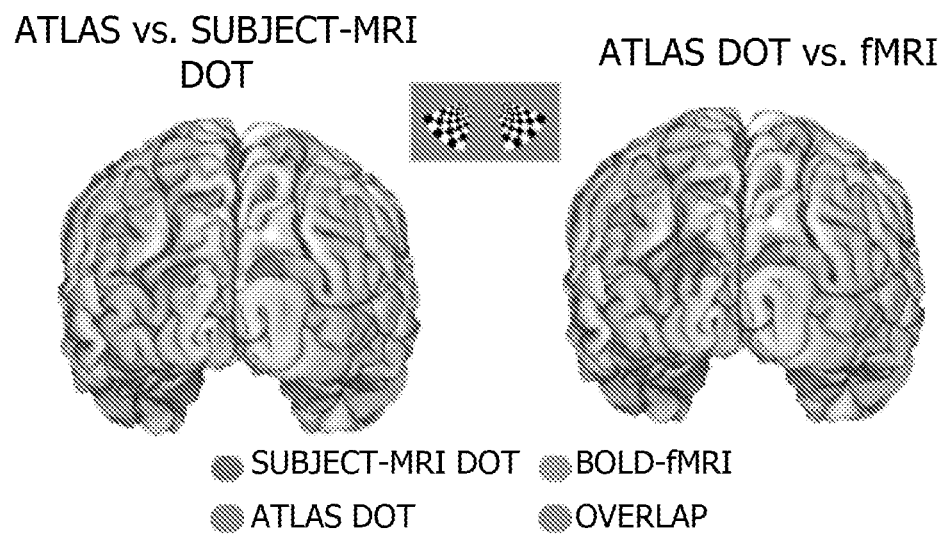
FIG. 10 is a diagram illustrating an example of atlas derived DOT visual activations on a single subject.

FIG. 10 is a diagram illustrating an example of atlas derived DOT visual activations on a single subject that spatially overlap with both individual MRI-based DOT reconstructions and fMRI activations (threshold at 50% maximum). In the example embodiment, the premise of atlas-based head modeling is validated using head surfaces extracted from subject MRI scans and by comparing to DOT reconstructions using subject-specific anatomical images and to subject-matched fMRI datasets.

An example modeling method described herein provides photometric head modeling for HD-DOT. Further, an example de-noising method is provided for motion de-noising for HD-DOT.

Figure 11:
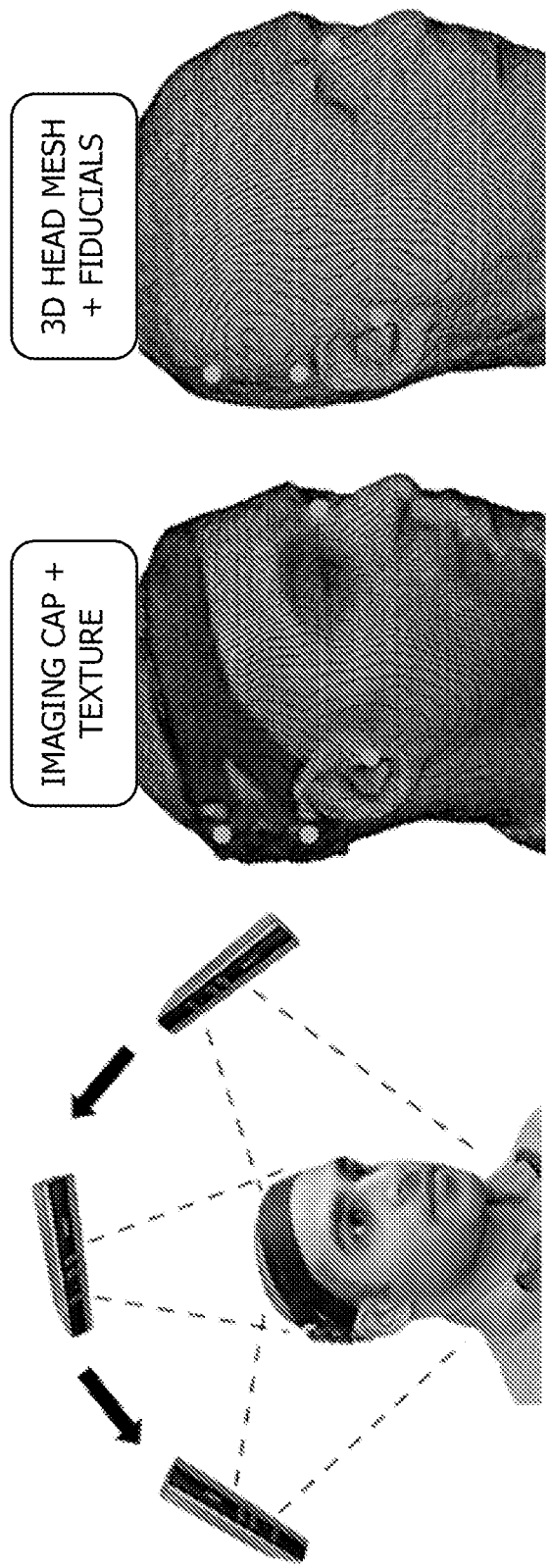
FIG. 11 is a diagram illustrating an example of real-time three-dimensional (3D) object scanning.
Figure 12:
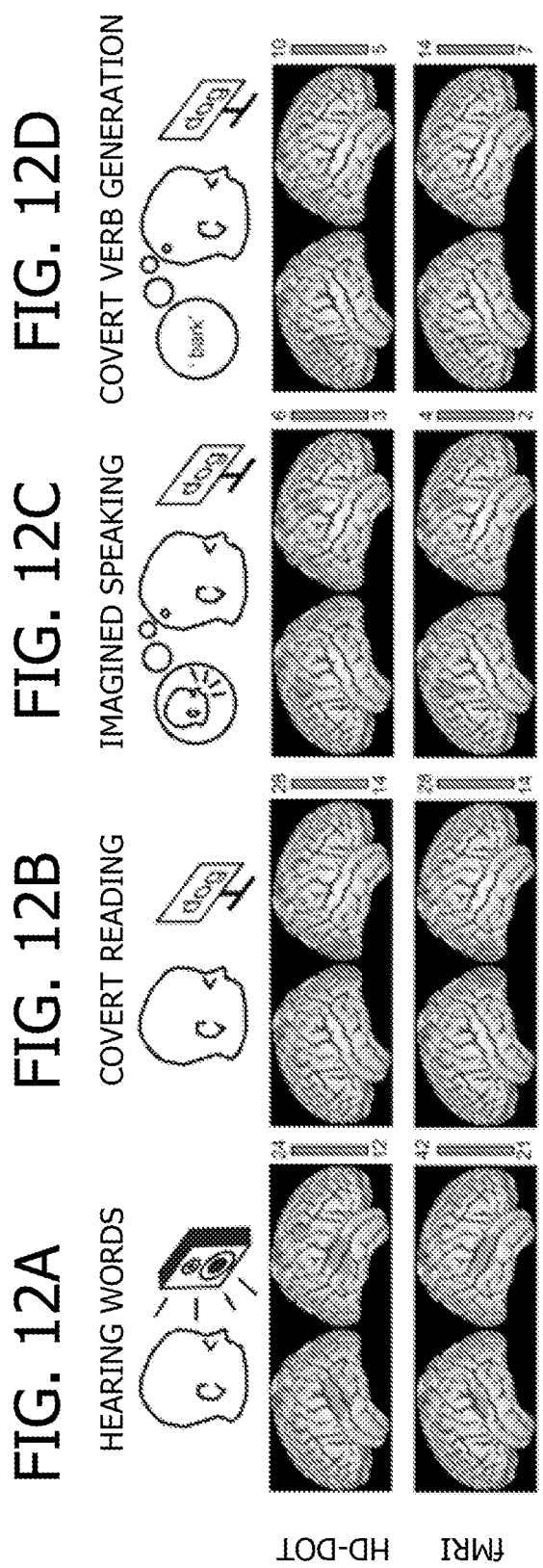
FIGS. 12A-12D are diagrams illustrating an example of a validation of functional diffuse optical tomography (fcDOT) in view of functional magnetic resonance imaging (fMRI) mapping of brain function using language paradigms.
Figure 13:
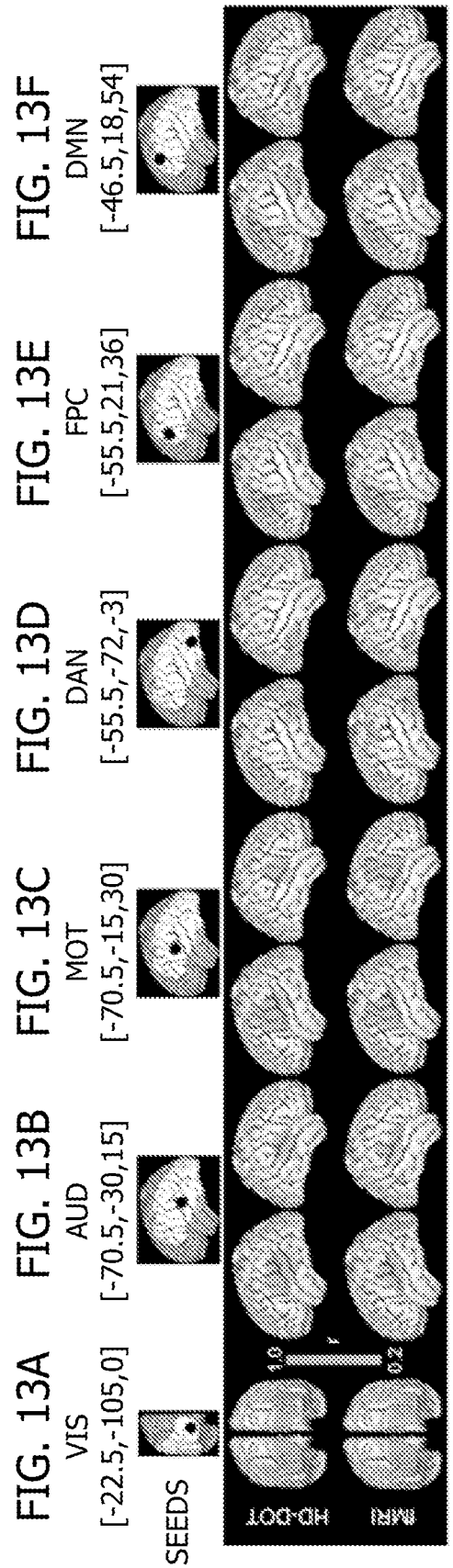
FIGS. 13A-13F are diagrams illustrating examples of resting state functional connectivity diffuse optical tomography (fcDOT) maps of distributed resting state networks.

For the acute care setting, it may be preferable to transform a reference head structure (e.g., atlas) to the subject's head surface shape, as a subject MRI is not always available. In the example modeling method (shown in FIGS. 9A-9E and 10), a set of anatomical fiducials measured on subject head surfaces are used to transform the reference head structure to the subject's head surface shape. Anatomical landmarks based on the 10/20 international system (including nasion, inion, pre-auricular points and Cz) are used for fiducials (shown in FIG. 11 with red dots). Moreover, selected optodes of the imaging array (shown in FIG. 11 with blue dots) are measured. In some known systems, fiducials are measured with an RF 3D digitizer (FastTrack, Polhemus USA). In the example modeling method, a photometric scanner (HandyScan 3D, Creaform) is used, providing improved speed over those known systems. The photometric scanner can retrieve both the 3D coordinates of optodes and the surface of the subject's head. To facilitate locating positions, reflective targets are placed onto the optode locations and anatomical fiducials. As shown in FIG. 11, feasibility of head surface capture is shown using a Kinect (Microsoft) camera. As shown in FIGS. 9A-9E and 10, the feasibility of using a two-step, linear then non-linear, transform method is established using surfaces extracted from MRI. In some cases, the example modeling method includes FEM head modeling for light propagation and inversion.

The accuracy of the example modeling method will be validated in control subjects with MRI. Performance will be evaluated in the physical space of the fibers (prior to image inversion) and also in image space with task responses at the subject and group level. Photometric capture will be evaluated against an RF 3D pen and physical rulers. It is contemplated that locational accuracy will be better than 1 mm. Further, it is contemplated that evaluations of functional response errors will follow some known methods. Yet further, it is contemplated that expected localization errors for atlas-derived versus subject-MRI based head models will be than about 2 mm (shown in FIG. 10), and between HD-DOT and fMRI will be less than about 6 mm. A study of healthy subjects (N=15) may optimize and validate (vs-MRI) the example modeling method.

Referring to the contemplated example de-noising method, frequently, data from clinical populations are contaminated with noise from movement artifacts. Effective noise suppression is needed so that large amounts of potentially useful data are not discarded. The example de-noising method includes a coupling coefficient (CC) motion noise removal method that leverages spatial structure in DOT data.

In principal, motion noise is specific to individual fibers (e.g., a head turn will press or pull optodes to/from the head). Motion changes the transmission to/from individual fibers and is a multiplicative noise factor. A wearable HD-DOT system may have about 3000 SD-pair measurements, yet only involve 288 fibers. In the example de-noising method, coupling coefficient errors are evaluated for baseline DOT reconstructions and the technique is extended to time variant data and coupling coefficients (the method transfers directly). An estimate of the coupling coefficients is calculated as the mean of the first nearest neighbor measurements for each source and detector. Time variant coupling coefficients are modeled as: $I_{cor}=[C_{so}/C_s(t)]*[C_{do}/C_d(t)]*I(t)$, where, $I(t)$ is a single SD-pair intensity, $I_{cor}(t)$ is the corrected intensity, $C_s(t)$ is the source coupling coefficient, $C_d(t)$ is the detector coupling coefficient, and $C_{so}$ and $C_{do}$ are the temporal mean of $C_s(t)$ and $C_d(t)$, respectively.

In some cases, the example de-noising method may include noise removal methods from fMRI and fNIRS. In particular, the example de-noising method may include one of four methods having shown promise for motion artifact removal: (i) independent component analysis (ICA); (ii) wavelet analysis; (iii) "scrubbing" data (cropping corrupted segments); and (iv) polynomial spline interpolation. Work with blind source separation of HD-DOT data suggests that ICA will also aide in noise identification and reduction.

The example de-noising method (and other noise reduction methods) will be evaluated in normal subjects (N=15). Task and resting state data will be collected with specific head motions (front-to-back, side-to-side, and twisting) programmed into an event design. Wireless accelerometers (G-link-LXRS, MicroStrain) will be used to measure head motion. The method will be assessed using four metrics: (a) the percent suppression of known movement artifact features; (b) the CNR of activation data; (c) test-retest reliability of resting state fc; and (d) the strength of short-vs-long distance connections. Based on known work on superficial-signal regression, expected improvements in data quality are the most dramatic when pre-correction CNR=3±2. Further, expected test-retest values are similar to, or better than, some known fcDOT (standard dev. of r<0.2 for homotopic connections).

Development of the methods for photometric head modeling and de-noising may benefit from feedback and iteration with the development of wearable, whole-head HD-DOT and the development of functional connectivity metrics, described later in detail. For example, instrument development may suggest approaches and/or demands for cap registration and photometry. Similarly, the success or challenges in the noise reduction methods may suggest refinements and/or alternatives to cap design. In one study, while the HandyScan 3D has accuracy specifications sufficient to meet a 1 mm goal, it is also possible that a Kinetic camera (with KinectFusion software) has sufficient resolution (shown in FIG. 11). The Kinect has the advantage of lower cost and may be more easily disseminated.

Studies were conducted to assess functional connectivity in healthy controls and chronic stroke, and to assess longitudinal functional connectivity in the acute care setting. While the low-frequency fluctuations in cerebral hemodynamics were detected by NIRS and reported in 2000, the spatial evaluation of the temporal cross-correlation was not explored until more recently. In a known case in 2008, an example of functional connectivity mapping using optical techniques was developed showing the feasibility of fcDOT in adult humans. In the known case, a large field-of-view (FOV) system was developed to make the first maps of distributed brain networks with fcDOT and the results were validated by comparison against fcMRI.

In assessing functional connectivity in healthy controls and chronic stroke, fcDOT methods are developed for evaluating how similar (or dissimilar) a single subject is in comparison to a population average. Specifically, fcDOT analyses are developed by compressing the full fc-matrix (voxel-by-voxel) down to images that assign an fc-metric to each voxel in the brain (shown in FIG. 14). For example, previous cases have found bilateral homotopic connectivity maps useful in mouse studies of Alzheimer's disease. Other potentially useful fc-indices include similarity and asymmetry measures. To test the fcDOT methods, normative data sets are acquired by studying healthy subjects within an anticipated age range (years 60-80). To establish the sensitivity of fcDOT to brain injury it will be important to validate in a population with a wide dynamic range in deficits. Chronic stroke patients have a large spectrum of temporally stable neurological deficits and thus provide the ideal patient population to evaluate fcDOT as a surrogate of neurological behavior exams.

In assessing longitudinal functional connectivity in the acute care setting, fcDOT is established in acute stroke. Bedside fcDOT (or fcDOT in the acute care setting) will enable longitudinal monitoring of functional connectivity. The wearability of fcDOT technology enables longitudinal bedside functional mapping of brain integrity during the post-stroke acute time window (12-72 hours) at the bedside in the intensive care unit (ICU). In validating bedside fcDOT in the ICU, fcDOT is compared to serial behavioral exams (e.g., the NIHSS). In some embodiments, the benefit of fcDOT as a brain monitoring imaging method is demonstrated in extended 12 hour scanning. Such time windows may be difficult or impossible with fcMRI.

In establishing fcDOT methods for mapping brain function in humans, some previous HD-DOT experiments had been limited to visual or motor task paradigms. To test HD-DOT imaging of distributed, multiple-order brain functions, a study was conducted following a known PET study and used a hierarchy of tasks to break down language into sensory (visual and auditory), articulatory (speaking), and semantic (higher order cognitive) processes (shown in FIGS. 12A-12D).

FIGS. 12A-12D are diagrams illustrating an example of a validation of fcDOT versus fMRI mapping of brain function using a plurality of language paradigms. FIG. 12A illustrates validating fcDOT versus fMRI in an example of using hearing words versus other words. FIG. 12B illustrates validating fcDOT versus fMRI using reading words versus other words. FIG. 12C illustrates validating fcDOT versus fMRI using imagined speaking versus reading. FIG. 12D illustrates validating fcDOT versus fMRI using converting verb generation versus imagined speaking.

In the examples of FIGS. 12A-12D, the contrast-to-noise-ratio (CNR, expressed as the max t-value associated with each color bar) for HD-DOT across subjects was within a factor of 2 of the fMRI CNR, suggesting that HD-DOT (within its FOV) has similar reproducibility to that of fMRI. A goal in extending the FOV was to image distributed resting state networks (RSNs) (shown in FIG. 13).

FIGS. 13A-13F are diagrams illustrating seed-based correlation maps obtained in normal volunteers for three sensory-motor and three cognitive networks, where the anatomical location of each seed is shown as a black dot. As shown in FIGS. 13A-13F, resting state functional connectivity of distributed networks provides a sensitive marker of neurological dysfunction. In particular, distributed RSNs may include the dorsal attention (DAN), fronto-parietal control (FPC) and default mode (DMN) networks. These fcDOT RSNs exhibit topographies similar to those obtained non-concurrently with fcMRI (FPC, DAN, DMN).

In assessing functional connectivity, a study was conducted to test the feasibility of a clinical HD-DOT system with limited FOV. FIGS. 14A-14I are diagrams illustrating examples of the feasibility of a clinical HD-DOT system with limited FOV. FIG. 14A illustrates fcDOT in the ICU on a patient recovering from an acute stroke. FIGS. 14B and 14C illustrate CT and fcDOT for a healthy subject. FIGS. 14D and 14E illustrate CT and fcDOT for a moderate stroke subject. FIGS. 14F and 14G illustrate CT and fcDOT for a severe stroke subject. As shown in FIGS. 14B, 14D, and 14F, the infarcts are represented by binary masks. The alterations in fc patterns measured via seed-voxel maps are correlated with the severity of stroke injury. As shown in FIG. 14H, an asymmetry index, a within subject measure, quantifies how different the maps are on opposite sides of the head and shows strong correlation to the NIHSS across 6 subjects. As shown in FIG. 14I, a similarity index, a between subject measure, quantifies how similar any two fc maps are and also shows a strong correlation to the NIHSS.

In the example embodiment, fcDOT is evaluated by validating fcDOT against fcMRI and neurocognitive testing in both a normal population and chronic stroke. More particularly, fcDOT is evaluated using fc-metrics that comprehensively evaluate the connection patterns including an asymmetry index and a similarity index. These metrics will also be used to compare fcDOT and fcMRI. A limited FOV HD-DOT system was developed to test the feasibility of imaging populations in the neonatal ICU and in the adult ICU at the bedside of patients recovering from stroke (shown in FIGS. 14A-14I).

Figure 14:
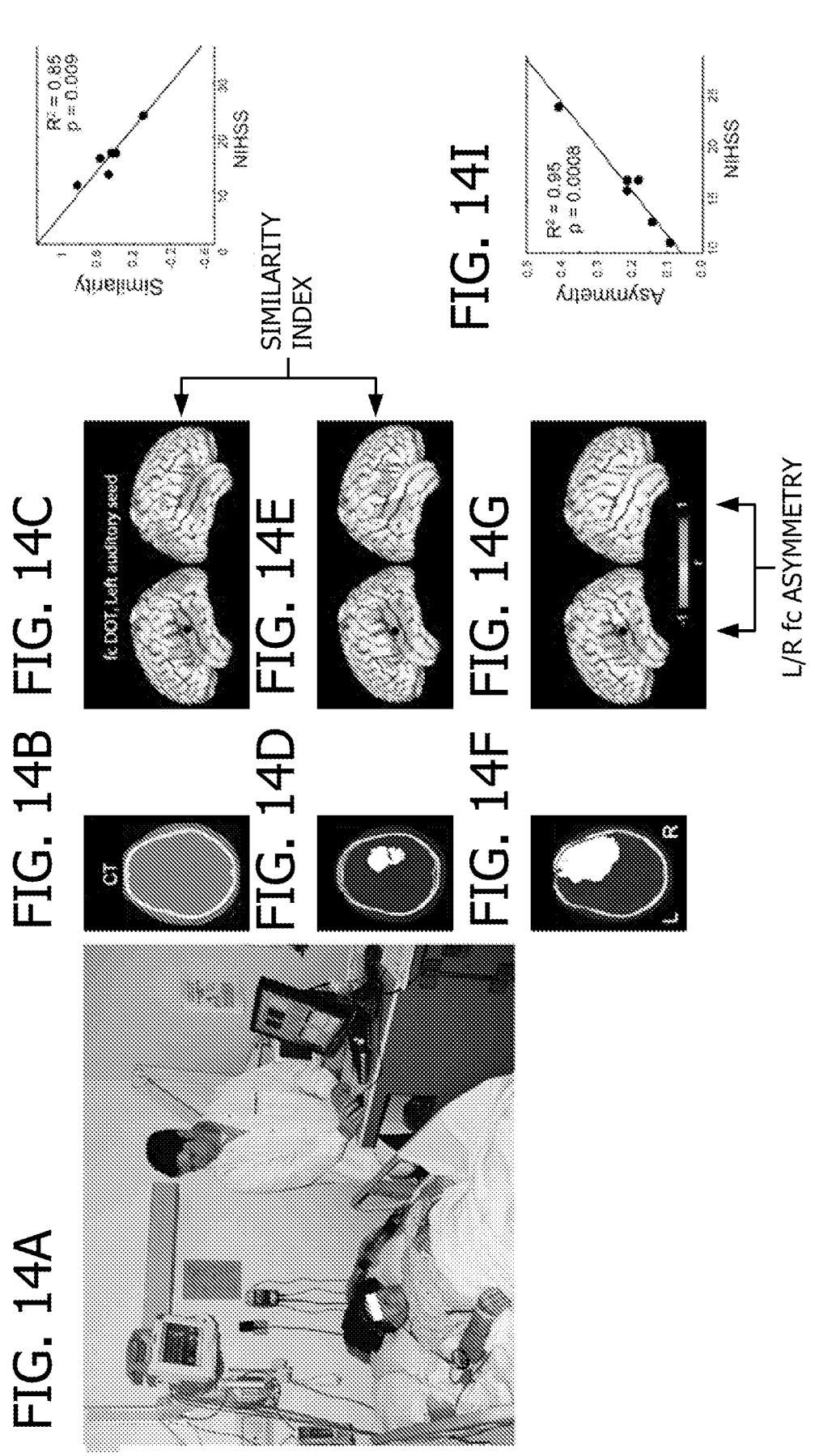
FIGS. 14A-14I are diagrams illustrating examples of a feasibility of a clinical HD-DOT system with limited field of view (FOV)

As shown in FIGS. 14C, 14E, and 14G, feasibility data in adult stroke patients with seeds placed in the temporal lobe display fcDOT maps whose disruption is significantly correlated with the volume of the infarct ($R^2=0.87$, $p=0.02$; N=5). The fc maps can be assessed for asymmetry between hemispheres within a subject and for similarity to healthy templates. Asymmetry is calculated as the percentage difference in number of voxels within a seed-based fc map between the left and right hemisphere. A comparison across 6 stroke subjects shows a correlation between a NIH Stroke Scale and asymmetry. As shown in FIG. 14$h$, subjects with worse (i.e., higher) NIHSS scores demonstrate greater asymmetry ($R^2=0.80$, $p=0.015$, uncorrected). In the example embodiment, fcDOT similarity was evaluated by calculating the spatial correlation between seed-voxel maps for a normal subject and each stroke subject. As shown in FIG. 14$i$, across the same 6 stroke subjects, the similarity index decreased as the NIHSS increased ($R^2=0.95$, $p=0.0008$, uncorrected).

In assessing functional connectivity, a study was conducted for continuous fcDOT in eight hour longitudinal scans in healthy subjects.

Figure 15:
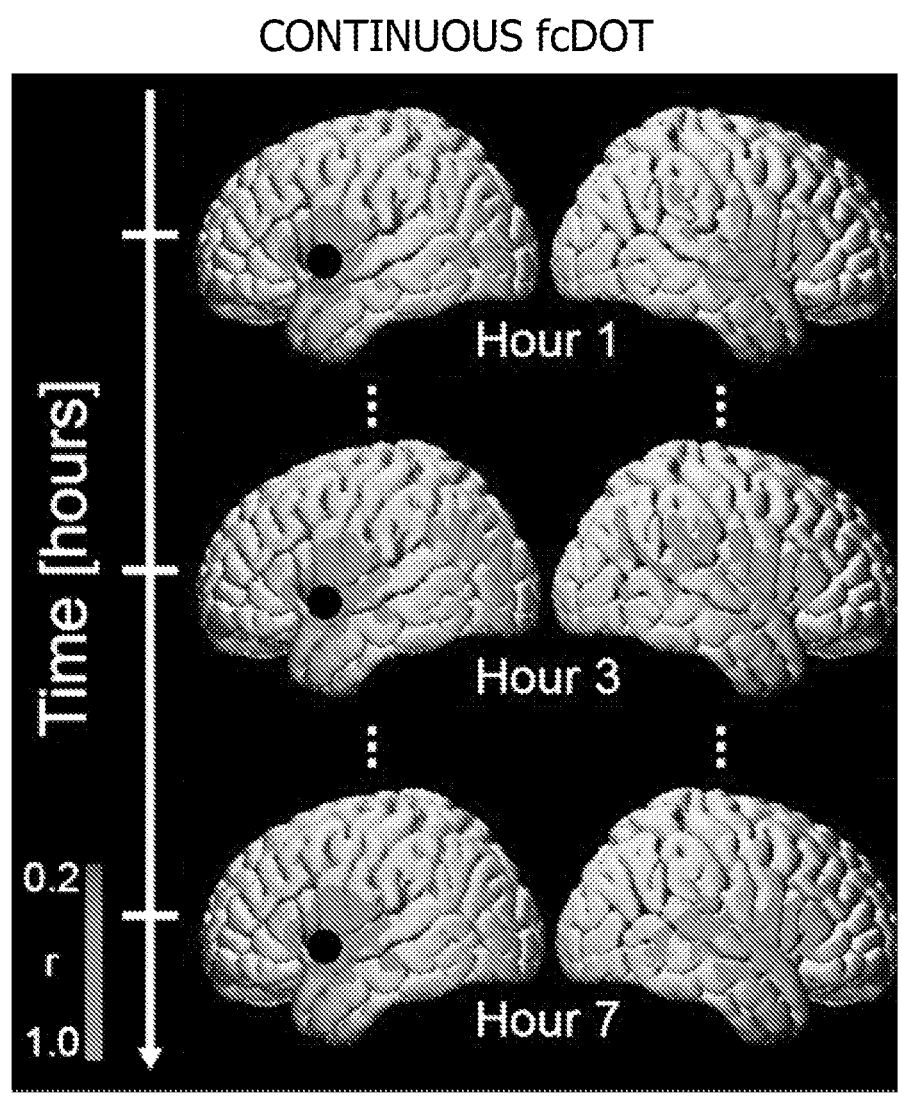
FIG. 15 is a diagram illustrating an example of longitudinal fcDOT maps.

FIG. 15 illustrates longitudinal fcDOT maps taken during a period of 7 hours. In determining the feasibility of imaging longitudinally, a group of 4 healthy subjects were scanned twice, each for 8 hours continuously. The first goal was to ascertain the wearability of the imaging cap. The subjects wear times were as follows: Subject 1, 7 h 47 min/7 h 21 min; Subject 2, 9 h 18 min/9 h 11 min; Subject 3, 8 h 10 min/8 h 40 min; Subject 4, 8 h 13 min/8 h 39 min. The four subjects were able to wear the cap for 8 hours (±30 min) without reporting any increased discomfort from the cap. This confirmed anecdotal evidence from shorter 2 hours scans, that any discomfort is evident during the first 30 minutes of scanning. When the initial cap fit is sufficiently optimized, the cap fit is wearable long-term. As shown in FIG. 15, preliminary image analysis shows promising stability of fcDOT across hours.

In further assessing functional connectivity, a study was conducted to develop fcDOT metrics for evaluating brain injury. To establish fcDOT sensitivity to brain injury a clinical population is sought with a wide dynamic range of functional deficits, stable injury and the potential for comparisons to fcMRI and behavior assays. Chronic stroke subjects fit these requirements.

In the study, inclusion criteria for healthy subjects (n=32) include: 1) age 50-80 years; 2) no history of neurological disorders; and 3) balanced for gender. Exclusion criteria include: HD-DOT headset discomfort or any MRI contraindications.

In the study, inclusion criteria for stroke subjects (n=48) include: 1) age 50-80 years and able to obtain informed consent from patient or patient's representative; 2) ischemic stroke (with or without thrombolytic therapy); 3) first time stroke; 4) patients are selected to stratify across a range of severities, NIHSS=5 to 25; and 5) time after stroke greater than 12 months. Exclusion criteria include: 1) non-stroke diagnosis; 2) intracerebral hemorrhage; 3) DOT cap discomfort; and 4) MRI contraindications.

Healthy subjects are imaged on two days with two sessions each day, including a total of one fcMRI session and three fcDOT sessions (in random order). Stroke subjects are also be brought in for two days, one day fcMRI and fcDOT, the other day fcDOT and behavior testing (in random order). Both days are within two weeks.

During each session, subjects are scanned (fcDOT) for 1.5 hours using (i) 30 min supine resting state, (ii) 30 min supine mixture of auditory stimuli (words) and visual stimuli (flickering checkerboards), and (iii) 30 min sitting 30° head-of-bed elevation.

For each subject, one 60 minute supine fMRI scan is obtained with (i) 30 minutes of resting state and (ii) 30 minutes of auditory and visual stimuli for validation of the fcDOT maps. fcMRI are collected by similar means to those shown in FIGS. 12A-12D and 13A-13F.

In evaluating behavior of stroke subjects, neurobehavioral assessments are conducted by a psychometrician blinded to the imaging results to comprehensively assess cognitive and motor deficits. Multiple cognitive domains are evaluated (e.g., language, memory, attention, and motor function) using the following tests: for spatial attention, a computerized Posner Task, recording reaction times (RTs) and accuracy; for motor, active range of motion at the wrist, grip strength, performance on the Action Research Arm Test (ARAT), speed on the Nine Hole Peg Test (NHPT), in pegs/second, gait speed, and Functional Independence Measurement (FIM) walk item; for attention, a Posner task, Mesulam symbol cancelation test, and Behavioral inattention test (BIT) star cancellation test; for memory, the Hopkins verbal learning test (HVLT) and brief visuospatial memory test (BVMT); for language, word comprehension, Boston Naming Test, oral reading of sentences, stem completion, and animal naming.

In the study, the fc-metrics computed for both fcDOT and fcMRI include seed-voxel maps, homotopic-fc, asymmetry-fc, and similarity-fc. Seed-voxel maps are computed using a subset of seeds from the fcMRI literature (within DOT FOV). Homotopic-fc is computed by constructing an inter-hemispheric homotopic index using every voxel in a hemisphere as a seed. In some embodiments, the homotopic connectivity metric strongly correlates with ischemic deficit. Asymmetry-fc is computed, for a given fc-map, by applying a threshold to binarize the fc map (e.g., r=0.5). The asymmetry index equals the normalized difference in the number of voxels above threshold between the hemispheres (shown in FIGS. 14A-14I). Similarity-fc is computed using a similarity index calculated for each voxel (seed), and measuring the spatial correlation between any two given fc maps (e.g., group-vs-group and subject-vs-group) (shown in FIGS. 14A-14I).

The performance of fcDOT in normal subjects is compared to fcMRI by validating head models, validating fcDOT against fcMRI, and comparing head-of-bed elevation. In validating head models, the reference head model is validated in the older controls. With the auditory and visual functional localizers, expected localization errors are 2 mm to 5 mm. Further, the fc-metrics are evaluated for the different head models at the subject and group level.

In validating fcDOT against fcMRI, fcDOT metrics are established through comparison to fcMRI and test-retest. The fcDOT data are validated through comparisons of between fcDOT and fcMRI at both the single subject and group level for the fc-metrics. In testing the reliability of each fcDOT metric, intra-class correlation coefficients (ICC) are computed for inter-session and intra-session comparisons.

In comparing head-of-bed elevation, the difference of fcDOT between supine and sitting 30° head-of-bed elevation is evaluated using means similar to validation of fcDOT against fcMRI, described previously. While there is no precedent from fcMRI, expected differences are relatively small, though likely detectable. In some embodiments, comparing head-of-bed elevation provides the control data for comparing the performance of fcDOT in chronic stroke to behavior.

In other cases, the performance of fcDOT in chronic stroke is compared to behavior. Hypothetically, fcDOT patterns in stroke patients differ from those of healthy age matched controls (shown in FIG. 10). The analysis for the performance of fcDOT in normal subjects is repeated for the stroke subject data. In addition, the behavioral metrics are compared against fc-metrics using logistic regression analysis to test whether behavior abnormalities in stroke are associated with fcDOT measures of dysfunction. Initial analysis may use global integrated neurological behavior measures (e.g., NIHSS) and global integrated measures of fcDOT (e.g., brain average of (dis)similarity metric). A secondary analysis may evaluate more specific functional relationships between the behavioral domains and sub-network fcDOT metrics (e.g., the average within sub-network strengths of somatomotor, attention visual and default mode sub-networks, shown in FIGS. 12 and 13). From known studies, it is anticipated that the somatomotor and default networks correlate with somatomotor behavior function. A linear mixed-model analysis is used on both behavioral and fc-indices. Control for the multiple comparisons follows known statistical analysis of HD-DOT and MRI, and uses a cluster analysis in conjunction with a random field noise model that incorporates measures of the local temporal and spatial correlations.

In other studies, other metrics for evaluating brain injury are developed. The field of fc-network analysis is rapidly advancing, and alternatives to the proposed fc-index may arise. For example, a method was developed for parcellating functional architecture. Other metrics may include measures derived from graph theory, e.g., node degree, community assignments, participation coefficient and between-ness centrality, cortical hubs and small world connectedness and dual regression. For example, regarding the proposed head model, a reference head may be used that incorporates anatomical aging and the shrinkage of brain, with age built either from a set of previous fcMRI stroke subjects.

In yet further assessing functional connectivity, an example study was conducted to test the feasibility of longitudinal fcDOT in the ICU. Acute stroke subjects test fcDOT in an acute disease in a subject population with a wide dynamic range of functional deficits and significant changes over a time (hours/days). Behavioral dysfunction ranges from a complete recovery to death. Temporally, following ischemic stroke, neurological status can be highly unstable. While fcDOT may eventually provide a more quantitative and continuous assay than current neurological exams, in the example embodiment, the NIH stroke scale (NIHSS) is used to evaluate fcDOT.

In some cases, in the study, a first method includes using a N=32 subjects, but with moderate 4 hour scans, during the first three days following stroke. In other cases, a second method may include a N=10 subjects, but pilot the feasibility of extended longitudinal imaging fcDOT for up to 12 hours.

In the study, for the first method, inclusion criteria include: 1) age 50-80 years and able to obtain informed consent from patient or patient's representative; 2) ischemic stroke (with or without thrombolytic therapy); 3) first time stroke; 4) patients will be selected to stratify across a range of severities, NIHSS=5 to 25; 5) first HD-DOT session within 12 hours of stroke onset. Exclusion criteria include: 1) non-stroke diagnosis; 2) intracerebral hemorrhage on recruitment; 3) HD-DOT headset discomfort.

In the study, for the second method, inclusion criteria include those for the first method, and also include patients who are under orders of 24 hour bed rest (e.g., all patients receiving thrombolytics or severe strokes), and excluding patients with significant aphasia (inability to communicate).

All stroke patients are evaluated in the Emergency Department (ED) by neurological examination, head CT, and standard laboratory tests. Following possible intravenous tissue plasminogen activator (IV tPA) infusion or mechanical (Solitaire stentriever) thrombolysis, patients are admitted to the Neurological-Neurosurgical ICU for post-treatment monitoring. The NIHSS and Glasgow Coma Scale (GCS, a 6-point clinical scale of arousal) is obtained every 2-4 hours as part of standard patient care.

In the study, for the first method, subjects (n=32) are imaged within 24 hours of stroke onset with two additional scans, once a day, obtained on subsequent hospital days (1-3). Using the DOT procedures previously described herein, scans last for 4 hours so that each imaging session spans either two or three NIHSS assessments. The reliability of fcDOT measures as indicators of stroke induced neurocognitive deficits is also evaluated.

In comparing fcDOT and NIHSS, it is hypothesized that metrics of fc disruption correlate with NIHSS. The fc metrics are paired with the concurrent NIHSS across all patients and time points (32 patients×3 imaging sessions×2 NIHSS time points=192 comparisons) to quantify the degree of correlation.

In detecting change in status over time, whereas the previous analysis groups all the data together (ignores timing), the first method of the example study tests if fcDOT can detect changes in neurological status over time. Patient improvement may follow reperfusion; deterioration may occur due to a number of causes including hemorrhage or cerebral edema. In patients with deteriorating neurologic status, fcDOT measures may degrade in parallel. This analysis leverages the multiple time epochs acquired within each subject.

In the study, for the second method, the full benefit of fcDOT as a brain monitoring imaging method is demonstrated in extended 12+ hours scanning Two small-scale studies are performed; first (n=5) scan for 8 hours, and second (n=5) scan for 12 hours. The study is restricted to subjects that can communicate so that the imaging cap may be removed if needed. Data analysis includes linear regression to NIHSS over time.

In some cases, fcDOT sensitivity may be established as an imaging biomarker for longitudinal monitoring of neurological status, e.g., to validate fcDOT in relation to NIHSS. For example, a study may compare fcDOT to CT. CT is used to define the spatial location and extent of infarct.

In other cases, fcDOT may have application in the ischemic stroke population. For example, fcDOT metrics may herald impeding herniation. Cytotoxic cerebral edema usually occurs within days after stroke onset, and is manifested by neurological deterioration and decline in level of arousal. Fc metrics may be able to detect early signs of edema, e.g., by correlating the disruption of contra-lesional local-fc with degree of edema as measured by midline shift (mm) from CT. Further, fcDOT may predict future functional outcome, since recent data suggests that bilateral homotopic fc is predictive of longer term outcome. Yet further, when sensitivity is high, further clinical studies to assess fcDOT utility in clinical decision-making (interventional rescue therapy in patients with "failed" IV tPA, or early craniectomy in patients with impending cerebral edema and midline shift) may be pursued.

Figure 16:
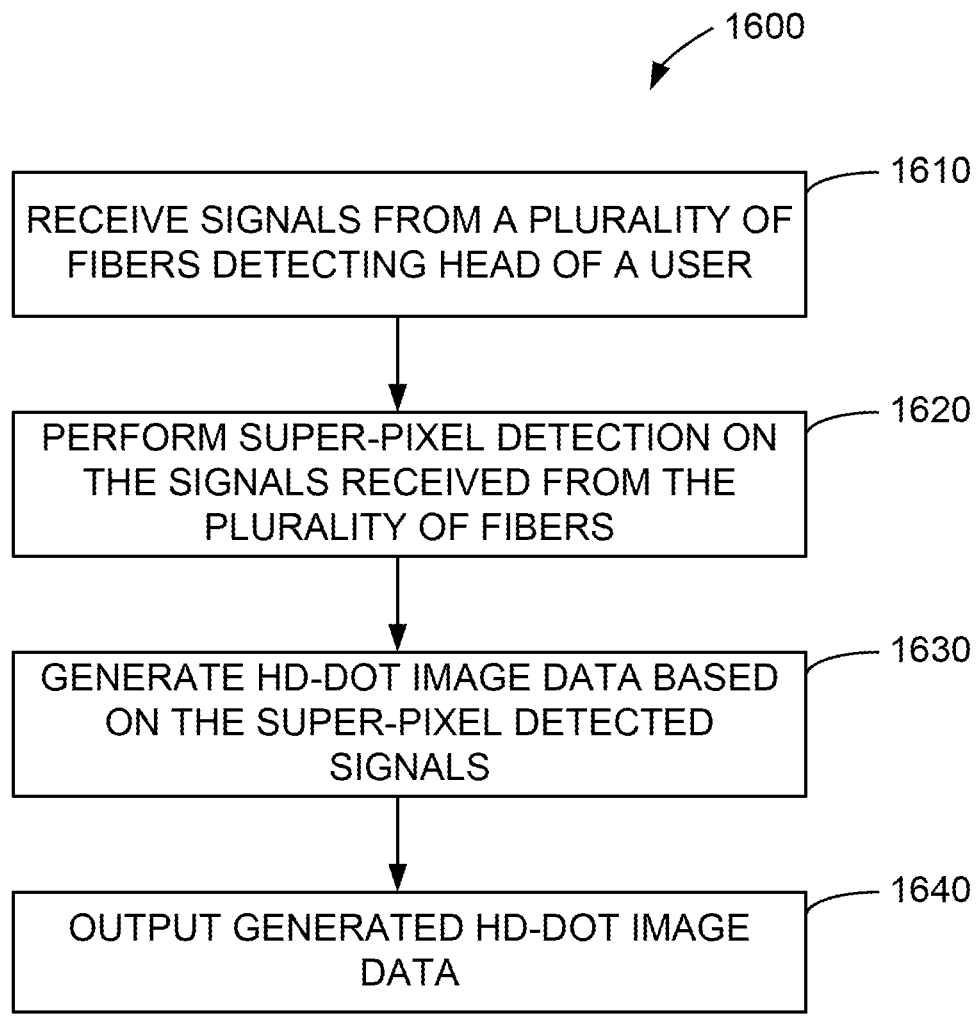
FIG. 16 is a diagram illustrating an example of a super-pixel detection method for measuring brain activity.

FIG. 16 is a diagram illustrating an example of a super-pixel detection method for measuring brain activity.

Referring to FIG. 16, method 1600 includes receiving a plurality of signals from a plurality of fibers detecting an image of a head of a user, in 1610. For example, each of the fibers may include a source fiber for emitting light towards the head of the user and a detector fiber for detecting light that is incident from the head of the user. T Furthermore, the plurality of fibers may be included in a fiber array. A first end of the fiber array may be attached to an imaging cap that is worn on a head of the user. The other end of the fiber array may be attached to an electronic console to measure signals detected from the imaging cap while worn on the head of the user.

The method 1600 further includes performing super-pixel detection on the image signals received from the plurality of fibers, in 1620. For example, rather than all pixels return individual imaging values, a detector may be divided into super-pixels. Each super-pixel may include a plurality of pixels, for example, 25×25 pixels, 40×40 pixels, 60×60 pixels, 85×85 pixels, and the like. Each super-pixel may include a core that is configured to sense light from the fibers included in the fiber array. Pixel values of pixels included in the core may be summed. Also, the core may be of any desired shape, for example, circular, square, elliptical, and the like. A buffer region may surround the core of each super-pixel. In the buffer region, light may decay thus preventing cross-talk between the super-pixels. Each super-pixel may further include a reference region that surrounds the buffer regions. The reference region may be used to detect stray light.

The method 1600 further includes generating HD-DOT image data based on the super-pixel detected image signals, in 1630. A detector may convert incident light into electron charges to generate an electric signal that may be processed and may be used to construct, for example, HD-DOT images of the patient or the patient's brain. In the example embodiment, the detector may include an electron multiply charge-coupled device (EMCCD) having a plurality of pixels defined on a surface of the detector. During operation, detector fibers transport light (i.e., scattered light received by the detectors) between an imaging cap and an electronic console. The received light may be focused onto detector by a lens, and the light incident on detector may be converted into an electric signal including HD-DOT image data The method 1600 further includes outputting the generated HD-DOT image data, in 1640. For example, the HD-DOT image data may be displayed on a screen that is electrically connected to the electronic console.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An electronic console for super-pixel detection and analysis, the electronic console comprising:
   a fiber array including a plurality of fibers configured to transport resultant light detected by a head apparatus worn by a subject;
   a detector coupled to the fiber array to detect resultant light from the plurality of fibers, the detector including an array of pixels, each pixel of the array of pixels being operable to detect light, the array of pixels being grouped into a plurality of super-pixels, each super-pixel including a different plurality of pixels of the array, each super-pixel associated with a fiber of the plurality of fibers, each super-pixel configured to generate a plurality of detection signals in response to resultant light from its associated fiber detected by its plurality of pixels at substantially a same time;
   a computing device coupled to the detector to receive the plurality of detection signals from each of the plurality of super-pixels, the computing device configured to generate a high density-diffuse optical tomography (HD-DOT) image signal of the brain activity of the subject based on the plurality of detection signals from each of the plurality of super-pixels; and
   a display configured to display the HD-DOT image signal of the brain activity of the subject.

2. The electronic console of claim 1, wherein the computing device further comprises a head modeling module configured to generate a photometric head model of the subject, wherein the computing device is configured to generate the HD-DOT image signal of the brain activity of the subject based at least in part on the generated photometric head model of the subject.

3. The electronic console of claim 1, wherein the computing device further comprises a de-noising module configured to remove noise from the plurality of detection signals, wherein the computing device is configured to generate the HD-DOT image signal of the brain activity of the subject based at least in part on the detection signals with the noise removed.

4. The electronic console of claim 1, wherein the detector comprises an electron multiply charge-coupled device (EMCCD) or a Complementary metal-oxide-semiconductor (CMOS) sensor.

5. The electronic console of claim 1, wherein each super-pixel is defined to include a core area including a plurality of core pixels, a buffer area including a plurality of buffer pixels surrounding the core, and a reference area including a plurality of reference pixels surrounding the buffer.

6. The electronic console of claim 5, wherein the plurality of detection signals include core signals generated by the plurality of core pixels, buffer signals generated by the plurality of buffer pixels, and reference signals generated by the plurality of reference pixels.

7. The electronic console of claim 6, wherein the computing device is configured to generate the HD-DOT image signal based on the core signals, configured to discard the buffer signals, and configured to calculate stray noise based at least in part on the reference signals.

8. The electronic console of claim 1, further comprising a fiber array holder configured to hold the plurality of fibers in a shape that corresponds to a shape of the detector to direct the resultant light of each fiber at a different super-pixel, and a lens configured to focus the resultant light from the plurality of fibers onto the detector.

9. The electronic console of claim 1, wherein the plurality of fibers comprise a plurality of source fibers configured to transport light to the head apparatus and a plurality of detector fibers configured to transport resultant light detected by the head apparatus.

10. A system comprising:
    a wearable head apparatus configured to be worn on a head of a subject, the head apparatus configured to direct light at the head of the subject and receive resultant light from the head of the subject in response to the light directed at the head of the subject; and
    an electronic console comprising:
    a fiber array including a plurality of fibers configured to transport light to the head apparatus worn by a subject and transport resultant light received by the head apparatus;
    a detector coupled to the fiber array to detect the resultant light from the plurality of fibers, the detector including an array of pixels, each pixel of the array of pixels being operable to detect light, the array of pixels being grouped into a plurality of super-pixels, each super-pixel including a different plurality of pixels of the array, each super-pixel associated with a fiber of the plurality of fibers, each super-pixel configured to generate a plurality of detection signals in response to resultant light from its associated fiber detected by its plurality of pixels at substantially a same time; and
    a computing device coupled to the detector to receive the plurality of detection signals from each of the plurality of super-pixels, the computing device configured to generate a high density-diffuse optical tomography (HD-DOT) image signal of the brain activity of the subject based on the plurality of detection signals from each of the plurality of super-pixels.

11. The system of claim 10, wherein the wearable head apparatus weighs between one half pound and one and one half pounds.

12. The system of claim 10, wherein the detector comprises an electron multiply charge-coupled device (EM- CCD) or a Complementary metal-oxide-semiconductor (CMOS) sensor that is configured to detect the resultant light from the plurality of fibers.

13. The system of claim 10, wherein each super-pixel is defined to include a core area including a plurality of core pixels, a buffer area including a plurality of buffer pixels surrounding the core, and a reference area including a plurality of reference pixels surrounding the buffer, wherein the plurality of detection signals include core signals generated by the plurality of core pixels, buffer signals generated by the plurality of buffer pixels, and reference signals generated by the plurality of reference pixels.

14. The system of claim 13, wherein the computing device is configured to generate the HD-DOT image signal based on the core signals, configured to discard the buffer signals, and configured to calculate stray noise based at least in part on the reference signals.

15. The system of claim 10, wherein the plurality of fibers comprise a plurality of source fibers configured to transport light to the wearable head apparatus worn by the subject and a plurality of detector fibers configured to transport resultant light detected by the wearable head apparatus.

16. A computer-implemented method for performing super-pixel detection using a detector that includes an array of pixels, each pixel of the array of pixels being operable to detect light, the array of pixels being grouped into a plurality of super-pixels, each super-pixel including a different plurality of pixels of the array, said method implemented by a computing device in communication with a memory, the method comprising:
receiving, by the computing device from the array of pixels, a plurality of detection signals detected at substantially a same time;
associating, for each super-pixel, a different subset of the plurality of detection signals with the super-pixel that generated the detection signals in the subset;
generating a high density-diffuse optical tomography (HD-DOT) image signal of the brain activity of the subject based at least in part on the subsets of the plurality of detection signals associated with the plurality of super-pixels; and
outputting the generated HD-DOT image signal.

17. The computer-implemented method of claim 16, further comprising generating a photometric head model of the subject, wherein the generating comprises generating the HD-DOT image signal of the brain activity of the subject is based at least in part on the photometric head model of the subject.

18. The computer-implemented method of claim 16, further comprising removing noise from the received plurality of detection signals.

19. The computer-implemented method of claim 16, wherein each super-pixel includes a core area including a plurality of core pixels, a buffer area including a plurality of buffer pixels surrounding the core, and a reference area including a plurality of reference pixels surrounding the buffer, wherein the plurality of detection signals include detection signals generated by the plurality of core pixels, detection signals generated by the plurality of buffer pixels, and detection signals generated by the plurality of reference pixels.

20. The computer-implemented method of claim 19, further comprising discarding the buffer signals, calculating stray noise based at least in part on the reference signals, and wherein the high density-diffuse optical tomography (HD-DOT) image signal of the brain activity of the subject is generated based on the core signals.

* * * * *